(12) United States Patent
Mody et al.

(10) Patent No.: US 6,638,924 B2
(45) Date of Patent: Oct. 28, 2003

(54) METALLOTEXAPHYRIN DERIVATIVES

(75) Inventors: Tarak D. Mody, Sunnyvale, CA (US); Joshua Galanter, Brookline, MA (US)

(73) Assignee: Pharmacyclics, Inc., Sunnyvale, CA (US)

( * ) Notice: Subject to any disclaimer, the term of this patent is extended or adjusted under 35 U.S.C. 154(b) by 0 days.

(21) Appl. No.: 09/941,924

(22) Filed: Aug. 28, 2001

(65) Prior Publication Data

US 2003/0073679 A1 Apr. 17, 2003

Related U.S. Application Data

(60) Provisional application No. 60/229,255, filed on Aug. 30, 2000.

(51) Int. Cl.$^7$ ................ A61K 31/409; C07D 487/22
(52) U.S. Cl. ................ 514/185; 514/410; 540/145; 540/465; 540/472; 534/10; 534/15; 534/16
(58) Field of Search ................ 540/145, 465, 540/472; 534/10, 15, 16; 514/185, 410

(56) References Cited

U.S. PATENT DOCUMENTS

| | | |
|---|---|---|
| 3,845,770 A | 11/1974 | Theeuwes et al. |
| 4,326,525 A | 4/1982 | Swanson et al. |
| 4,902,514 A | 2/1990 | Barclay |
| 4,935,498 A | 6/1990 | Sessler |
| 4,992,445 A | 2/1991 | Lawter et al. |
| 5,001,139 A | 3/1991 | Lawter et al. |
| 5,011,472 A | 4/1991 | Aebischer et al. |
| 5,023,252 A | 6/1991 | Hseih |
| 5,041,078 A | 8/1991 | Matthews et al. |
| 5,120,411 A | 6/1992 | Sessler et al. |
| 5,159,065 A | 10/1992 | Sessler et al. |
| 5,162,509 A | 11/1992 | Sessler et al. |
| 5,252,720 A | 10/1993 | Sessler et al. |
| 5,256,399 A | 10/1993 | Sessler et al. |
| 5,272,142 A | 12/1993 | Sessler et al. |
| 5,292,414 A | 3/1994 | Sessler et al. |
| 5,302,714 A | 4/1994 | Sessler et al. |
| 5,369,101 A | 11/1994 | Sessler et al. |
| 5,432,171 A | 7/1995 | Sessler et al. |
| 5,439,570 A | 8/1995 | Sessler et al. |
| 5,451,576 A | 9/1995 | Sessler et al. |
| 5,457,183 A | 10/1995 | Sessler et al. |
| 5,457,195 A | 10/1995 | Sessler et al. |
| 5,475,104 A | 12/1995 | Sessler et al. |
| 5,504,205 A | 4/1996 | Sessler et al. |
| 5,525,325 A | 6/1996 | Sessler et al. |
| 5,530,123 A | 6/1996 | Sessler et al. |
| 5,543,123 A | 8/1996 | Hofmann et al. |
| 5,559,207 A | 9/1996 | Sessler et al. |
| 5,565,552 A | 10/1996 | Magda et al. |
| 5,567,687 A | 10/1996 | Magda et al. |
| 5,569,759 A | 10/1996 | Sessler et al. |
| 5,580,543 A | 12/1996 | Sessler et al. |
| 5,583,220 A | 12/1996 | Sessler et al. |
| 5,587,371 A | 12/1996 | Sessler et al. |
| 5,587,463 A | 12/1996 | Sessler et al. |
| 5,591,422 A | 1/1997 | Hemmi et al. |
| 5,594,136 A | 1/1997 | Sessler et al. |
| 5,595,726 A | 1/1997 | Magda et al. |
| 5,599,923 A | 2/1997 | Sessler et al. |
| 5,599,928 A | 2/1997 | Hemmi et al. |
| 5,601,802 A | 2/1997 | Hemmi et al. |
| 5,607,924 A | 3/1997 | Magda et al. |
| 5,616,345 A | 4/1997 | Geoghegan et al. |
| 5,622,946 A | 4/1997 | Sessler et al. |
| 5,672,490 A | 9/1997 | Sessler et al. |
| 5,714,328 A | 2/1998 | Magda et al. |
| 5,775,339 A | 7/1998 | Woodburn et al. |
| 5,776,925 A | 7/1998 | Young et al. |
| 5,798,491 A | 8/1998 | Magda et al. |
| 5,801,229 A | 9/1998 | Sessler et al. |
| 5,955,586 A | 9/1999 | Sessler et al. |
| 6,022,526 A | 2/2000 | Woodburn et al. |
| 6,022,959 A | 2/2000 | Magda et al. |

FOREIGN PATENT DOCUMENTS

| | | |
|---|---|---|
| WO | WO 90/10633 | 9/1990 |
| WO | WO 94/09003 | 4/1994 |
| WO | WO 94/29316 | 12/1994 |
| WO | WO 95/10307 | 4/1995 |
| WO | WO 95/21845 | 8/1995 |
| WO | WO 96/09315 | 3/1996 |
| WO | WO 96/38461 | 12/1996 |
| WO | WO 96/40253 | 12/1996 |
| WO | WO 97/26915 | 7/1997 |
| WO | WO 97/35617 | 10/1997 |
| WO | WO 97/46262 | 12/1997 |
| WO | WO 98/07733 | 2/1998 |
| WO | WO 00/01413 | 1/2000 |

OTHER PUBLICATIONS

Garini, et al., *Spectral Bioimaging*, John Wiley & Sons, NY:NY, (1996), pp. 87–124.

Rockwell, et al., Growth and Cell Population Kinetics of Single and Multiple KHT Sarcomoas, *Cell Tissue Kinetics*, (1972), vol. 1, pp. 449–457.

*Primary Examiner*—Richard L. Raymond
(74) *Attorney, Agent, or Firm*—Morrison & Foerster LLP

(57) ABSTRACT

Novel derivatives of metallotexaphyrins are prepared by modifying the apical ligands associated with the central metal component of a metallotexaphyrin.

37 Claims, No Drawings

METALLOTEXAPHYRIN DERIVATIVES

CROSS REFERENCE TO RELATED APPLICATIONS

This application claims the benefit of U.S. Patent Application Ser. No. 60/229,255, filed Aug. 30, 2000, the disclosure of which is incorporated herein by reference in its entirety.

FIELD OF THE INVENTION

The present invention relates to methods for modifying metallotexaphyrins to provide metallotexaphyrin derivatives (MTDs) having a wide range of physicochemical properties. In particular, the methods involve modifying the apical ligands associated with the central metal component of metallotexaphyrins. The invention also relates to the novel MTDs prepared by these methods, and their uses, and pharmaceutical compositions containing such compounds.

BACKGROUND INFORMATION

Porphyrins, the so-called "expanded porphyrins", and related polypyrrole structures are members of a class of macrocycles capable of forming stable complexes with metals. The metal is constrained (as its cation) within a central binding cavity of the macrocycle (the "core"). The anions associated with the metal cation are found above and below the core; and are called apical ligands. Examples of this class of macrocycles are porphyrins, porphyrin isomers, porphyrin-like macrocycles, benzoporphyrins, texaphyrins, alaskaphyrins, sapphyrins, rubyrins, porphycenes, chlorins, benzochlorins, and purpurins.

One preferred class of macrocycles is the texaphyrins. Texaphyrins are aromatic pentadentate macrocyclic compounds that have the ability to integrate metals within their core to form complexes known as "metallotexaphyrins". Texaphyrins and metallotexaphyrins have been described as being useful as MRI contrast agents, fluorescent imaging agents for cancer, plaque, and retinal diseases, as radiosensitizers and as chemosensitizers in both oncology and atherosclerosis, and as photosensitizers in photodynamic therapy in oncology, atherosclerosis, and ophthamology. They have also been described as having the ability to hydrolytically cleave phosphate esters such as RNA, and to photolytically cleave RNA and DNA. Texaphyrins are aromatic benzannulene compounds containing both 18$\pi$- and 22$\pi$-electron delocalization pathways. Texaphyrin molecules absorb light strongly in the tissue-transparent 700–900 nm range, and they exhibit selective uptake (or biolocalization) in certain tissues, particularly regions such as liver, atheroma or tumor tissue, and neovascularized regions. Such selectivity can be detected by magnetic resonance imaging (for example with paramagnetic metal complexes) and by fluorescence.

Accordingly, advantage may be taken of this property to provide a means for selectively treating tumors, plaque caused by atherosclerosis, retinal diseases, and the like, as disclosed in the publications incorporated by reference below in the detailed description of the invention. Notwithstanding these properties, it has remained desired to provide new MTDs having a range of physicochemical properties, such, as improved solubility and/or lipophilicity, lower toxicity, and improved stability, but still retaining the basic attribute of selective localization.

One method of accomplishing these goals would be to change the properties of existing metallotexaphyrins by modifying the functional groups covalently attached to the macrocycle, and/or by changing the core metal. However, preparations of such MTDs require complicated syntheses, since each compound is necessarily made by a different synthetic route, and/or is derived from different starting materials. Accordingly, there remains a need for a convenient method for preparing a library of texaphyrin derivatives, which vary in their physicochemical properties, and can be synthesized easily and efficiently in high yield. The present invention provides such a method by modifying the apical ligands associated with the metal component of existing metallotexaphyrins to provide a library of MTDs having a wide range of physicochemical properties.

SUMMARY OF THE INVENTION

It is an object of this invention to provide novel metallotexaphyrin derivatives (MTDs). Accordingly, in a first aspect, the invention relates to compounds having the Formula I:

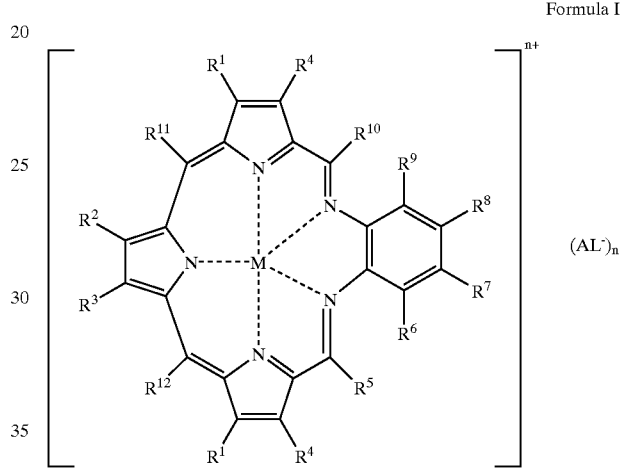

Formula I wherein:
M is a metal cation;
AL is an apical ligand;
with the proviso that AL is not derived from acetic acid, nitric acid, or hydrochloric acid; n is an integer of 1–5;
$R^1$, $R^2$, $R^3$, $R^4$, $R^5$, $R^6$, $R^8$, and $R^9$ are independently chosen from the group consisting of hydrogen, halogen, hydroxyl, optionally substituted alkyl, optionally substituted alkenyl, optionally substituted alkynyl, optionally substituted aryl, optionally substituted heteroaryl, nitro, acyl, optionally substituted alkoxy, alkylalkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and;
$R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl; with the proviso that: halogen is other than iodide and haloalkyl is other than iodoalkyl.

Substituents $R^1$–$R^{12}$ are further described in U.S. patents, PCT publications and allowed and pending patent applications, incorporated by reference in the Detailed Description.

M can be monovalent, divalent, trivalent, or tetravalent. Examples of monovalent metal cations are tellurium and technetium; an example of an appropriate tetravalent metal is thorium. Preferred are divalent and trivalent metals. Preferred divalent metal cations are Ca(II), Mn(II), Co(II), Ni(II), Zn(II), Cd(II), Hg(III), Fe(II), Sm(II), or U(II). Preferred trivalent metal cations are Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), or U(III). More preferred trivalent metal cations are Lu(III) or Gd(III). In some embodiments, in particular for use in neutron capture therapy, the metal can be present as a pure isotope of the metal, or be enriched in one or more of its isotopes. For example, gadolinium may be present as its $^{155}$Gd or $^{157}$Gd isotope, or "natural" gadolinium may be optionally enriched in the isotopes $^{155}$Gd and/or $^{157}$Gd. Similarly, cadmium may be present as the cadmium isotope $^{113}$Cd, or "natural" cadmium enriched in $^{113}$Cd; europium may be present as the europium isotope $^{115}$Eu, or "natural" europium enriched in $^{151}$Eu; mercury may be present as the mercury isotope $^{199}$Hg, or "natural" mercury enriched in $^{199}$Hg; and samarium may be present as the samarium isotope $^{149}$Sm, or "natural" samarium enriched in $^{149}$Sm. Particularly preferred for neutron capture therapy is the $^{157}$Gd isotope of gadolinium, or "natural" gadolinium enriched in the isotope $^{157}$Gd.

M or one of groups $R^1$ to $R^{12}$ can be radioactive, and are as described in the U.S. patents, PCT publications, and allowed and pending patent applications disclosed and incorporated by reference below.

Preferred apical ligands are formed, for example, from carboxylates of sugar derivatives, such as gluconic acid or glucoronic acid, cholesterol derivatives such as cholic acid and deoxycholic acid, polyethylene glycol (PEG) acids, or carboxylic acid derivatives, such as formic acid, propionic acid, butyric acid, pentanoic acid, methylvaleric acid, glycolic acid, pyruvic acid, oxalic acid, malic acid, malonic acid, succinic acid, maleic acid, fumaric acid, tartaric acid, 3,6,9-trioxodecanoic acid, 3,6-dioxoheptanoic 2,5-dioxoheptanoic acid, citric acid, benzoic acid, cinnamic acid, mandelic acid, salicylic acid. Other preferred acids for forming apical ligands include methanesulfonic acid, ethanesulfonic acid, p-toluene-sulfonic acid, organophosphates, such as methylphosphonic acid and phenylphosphonic acid, phosphoric acid and the like.

A second aspect of the present invention relates to a preferred process for synthesizing MTDs of Formula I, comprising the steps of contacting the desired apical ligand with an quartenary amine resin (e.g., Ambersep 900(OH), Amberlite IRA904), contacting the apical ligand/amino acid resin complex thus produced with a metallotexaphyrin, preferably a metallotexaphyrin acetate, and isolating the MTD of Formula I having the desired novel apical ligand.

A third aspect of the present invention relates to an alternative process for synthesizing MTDs of Formula I, comprising the steps of contacting a metallotexaphyrin, preferably as an acetate, with a large excess of the chosen apical ligand, optionally heating the mixture, and isolating the MTD of Formula I containing the novel apical ligand.

A fourth aspect of the present invention relates to a process for synthesizing MTDs having a mixture of apical ligands, comprising the steps of contacting a metallotexaphyrin, preferably a metallotexaphyrin acetate, with a mixture of apical ligands, optionally heating the mixture, and isolating the MTD of Formula I containing a mixture of apical ligands. Alternatively, the reaction can be carried out in a biphasic fashion (for example, in a methylene chloride/water mixture).

A fifth aspect of this invention relates to pharmaceutical formulations, comprising a therapeutically effective amount of an MTD of Formula I and at least one pharmaceutically acceptable excipient.

A sixth aspect of this invention relates to a method of using the MTDs of Formula I in the treatment of a disease or condition in a mammal that results from the presence of neoplastic tissue, which method comprises administering to a such a mammal a therapeutically effective amount of an MTD of Formula I, and optionally treating further with a chemotherapeutic compound, or preferably treating the area in proximity to the neoplastic tissue with a therapeutic energy means. Preferred therapeutic energies include photoirradiation, ionizing radiation, ultrasound, and neutron bombardment.

A seventh aspect of this invention relates to a method of using the MTDs of Formula I in the treatment of a disease or condition in a mammal that results from the presence of atherosclerosis, which method comprises administering to a such a mammal a therapeutically effective amount of an MTD of Formula I, and treating the area in proximity to the plaque caused by atherosclerosis with a therapeutic energy means. Preferred therapeutic energies include photoirradiation, ionizing radiation, ultrasound, and neutron bombardment.

An eighth aspect of this invention relates to a method of using the MTDs of Formula I in the treatment of a disease or condition in a mammal that results from areas of neovascularization, in particular age-related ocular degeneration, which method comprises administering to a such a mammal a therapeutically effective amount of an MTD of Formula I, and treating the area in proximity to the neovascularization with a therapeutic energy means. Preferred therapeutic energies include photoirradiation, ionizing radiation, ultrasound, and neutron bombardment.

DETAILED DESCRIPTION OF THE INVENTION

This invention provides novel metallotexaphyrin derivatives (MTDs) having a wide range of physicochemical and biological properties, and methods of making them. In particular, the invention provides a method of exchanging the existing apical ligands of a metallotexaphyrin with one or more different apical ligands. The apical ligand exchange modifies the properties of the metallotexaphyrin by altering, for example, its solubility, solution pH, partition coefficient, or other physicochemical properties. Changing the pharmacokinetics and/or the biodistribution of the complex in this fashion may result in, for example, better clearance and/or selective uptake in various tissues, such as tumor tissue, or atheromatous plaque.

For example, greater solubility of the MTD when placed in a physiologically compatible buffer can be expected to give greater serum concentration that can be obtained in vivo. This is useful, for example, in delivering the MTD directly to the area of plaque by intra-arterial injection, in which case higher uptake can be achieved. Additionally, higher solubility leads to lower aggregation effects, which provides lower in-vivo toxicity.

In particular, gluconate or glucoronate apical ligands render the MTDs very soluble, and are consequently useful for indications that call for higher plasma concentrations of the MTD. The higher solubility of such compounds, as noted above, provides greater potential for tumor uptake of the compounds of the invention. Alternatively, cholate or deoxycholate ligands decrease the compound's solubility and impart hydrophobicity. Hydrophobic compounds, when enclosed in a lipid vacuole, are useful for alternative delivery routes such as oral and topical administration. Additionally, by changing to amphiphilic apical ligands such as PEG acids, the MTDs of the invention can be made soluble in a wide variety of solvents.

The existing apical ligands of a metallotexaphyrin can be exchanged for a wide range of different apical ligands, including mono or polyanionic ligands, such as carboxylates of sugar derivatives and cholesterol derivatives, PEG acids, organic acids, organosulfates, organophosphates, or phosphates or other inorganic ligands.

It should be noted that metallomacrocycles other than metallotexaphyrins can be modified in the same manner as summarized above. That is, metallomacrocycle derivatives can be prepared from metallomacrocycles in a manner similar to those disclosed herein. Examples of macrocycles from which metallomacrocylee derivative can be made are porphyrins, porphyrin isomers, porphyrin-like macrocycles, benzoporphyrins, alaskaphyrins, sapphyrins, rubyrins, porphycenes, chlorins, benzochlorins, and purpurins.

Definitions and General Parameters

As used in the present specification, the following words and phrases are generally intended to have the meanings as set forth below, except to the extent that the context in which they are used indicates otherwise.

The term "alkyl" refers to a monoradical branched or unbranched saturated hydrocarbon chain preferably having from 1 to 20 carbon atoms, more preferably 1 to 10 carbon atoms, and even more preferably 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to
1) an alkyl group as defined above, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO—alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or
2) an alkyl group as defined above that is interrupted by 1–20 atoms independently chosen from oxygen, sulfur and NR$^a$—, where R$^a$ is chosen from hydrogen, or optionally substituted alkyl, cycloalkyl, alkenyl, cycloalkenyl, alkenyl, cycloalkenyl, alkynyl, aryl, heteroaryl and heterocyclic; or
3) an alkyl group as defined above that has both from 1 to 5 substituents as defined above and is also interrupted by 1–20 atoms as defined above.

One preferred alkyl substituent is hydroxy, exemplified by hydroxyalkyl groups, such as 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like.

The term "alkylene" refers to a diradical of a branched or unbranched saturated hydrocarbon chain, preferably having from 1 to 20 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$—and —CH(CH$_3$)CH$_2$—) and the like.

The term "substituted alkylene" refers to:
(1) an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where two substituents on the alkylene group are fused to form one or more cycloalkyl, substituted cycloalkyl, cycloalkenyl, substituted cycloalkenyl, aryl, heterocyclic or heteroaryl groups fused to the alkylene group; or
(2) an alkylene group as defined above that is interrupted by 1–20 atoms independently chosen from oxygen, sulfur and NR$^1$—, where R$^a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or
(3) an alkylene group as defined above that has both from 1 to 5 substituents as defined above and is also interrupted by 1–20 atoms as defined above.

Examples of substituted alkylenes are chloromethylene (—CH(Cl)—), aminoethylene (—CH(NH$_2$)CH$_2$—), methylaminoethylene ((—CH(NHMe)CH$_2$—), 2-carboxypropylene isomers (—CH$_2$CH(CO$^2$H)CH$_2$—), ethoxyethyl (—CH$_2$CH$^2$O—CH$_2$CH$_2$—), ethylmethylaminoethyl (—CH$_2$CH$_2$N(CH$_3$)CH$_2$CH$_2$—), 1-ethoxy-2-(2-ethoxy—ethoxy)ethane (—CH$_2$CH$_2$O—CH$_2$CH$_2$—OCH$_2$CH$_2$—OCH$_2$CH$_2$—), and the like.

The term "alkaryl" refers to the groups-optionally substituted alkylene-optionally substituted aryl, where alkylene, substituted alkylene, aryl and substituted aryl are defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O—and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to the groups substituted alkyl-O—, substituted alkenyl-O—, substituted cycloalkyl-O—, substituted cycloalkenyl-O—, and substituted alkynyl-O—where substituted alkyl, substituted alkenyl, substituted cycloalkyl, substituted cycloalkenyl and substituted alkynyl are as defined herein. One preferred substituted alkoxy group is substituted alkyl-O, and includes groups such as —OCH$_2$CH$_2$OCH$_3$, PEG groups such as —O(CH$_2$CH$_2$O)$_x$CH$_3$, where x is an integer of 2–20, preferably 2–10, and more preferably 2–5. Another preferred substituted alkoxy group is —O—CH$_2$—(CH$_2$)$_y$—OH, where y is an integer of 1–10, preferably 1–4.

The term "alkylalkoxy" refers to the groups -alkylene-O—alkyl, alkylene-O-substituted alkyl, substituted alkylene-O-alkyl and substituted alkylene-O-substituted alkyl wherein alkyl, substituted alkyl, alkylene and substituted alkylene are as defined herein. Preferred alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Preferred alkylthioalkoxy groups are alkylene-S-alkyl and include, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkenyl" refers to a monoradical of a branched or unbranched unsaturated hydrocarbon group preferably having from 2 to 20 carbon atoms, more preferably 2 to 10 carbon atoms and even more preferably 2 to 6 carbon atoms and having at least 1 and preferably from 1–6 sites of vinyl unsaturation. Preferred alkenyl groups include ethenyl (—CH=CH$_2$), 1-propylene (—CH$_2$CH=CH$_2$), isopropylene (—C(CH$_3$)=CH$_2$), and the like.

The term "substituted alkenyl" refers to an alkenyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical of a branched or unbranched unsaturated hydrocarbon group preferably having from 2 to 20 carbon atoms, more preferably 2 to 10 carbon atoms and even more preferably 2 to 6 carbon atoms and having at least 1 and preferably from 1–6 sites of vinyl unsaturation. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined above having from 1 to 5 substituents, and preferably from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkynyl" refers to a monoradical of an unsaturated hydrocarbon, preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynyl groups include ethynyl, (—C≡CH), propargyl (or propynyl, —C≡CCH$_3$), and the like.

The term "substituted alkynyl" refers to an alkynyl group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 20 carbon atoms, more preferably 2 to 10 carbon atoms and even more preferably 2 to 6 carbon atoms and having at least 1 and preferably from 1–6 sites of acetylene (triple bond) unsaturation. Preferred alkynylene groups include ethynylene (—C≡C—), propargylene (—CH$_2$—C≡C—) and the like.

The term "substituted alkynylene" refers to an alkynylene group as defined above having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acyl" refers to the groups HC(O)—, alkyl-C(O)—, substituted alkyl-C(O)—, cycloalkyl-C(O)—, substituted cycloalkyl-C(O)—, alkenyl-C(O)—, substituted alkenyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" or "aminocarbonyl" refers to the group —C(O)NRR where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocyclic group of from 6 to 20 carbon atoms having a single ring (e.g., phenyl) or multiple condensed (fused) rings (e.g., naphthyl or anthryl). Preferred aryls include phenyl, naphthyl and the like.

Unless otherwise constrained by the definition for the aryl substituent, such aryl groups can optionally be substituted with from 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The term "aryloxy" refers to the group aryl-O— wherein the aryl group is as defined above including optionally substituted aryl groups as also defined above.

The term "arylene" refers to the diradical derived from aryl (including substituted aryl) as defined above and is exemplified by 1,2-phenylene, 1,3-phenylene, 1,4-phenylene, 1,2-naphthylene and the like.

The term "amino" refers to the group —NH$_2$.

The term "substituted amino refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl and heterocyclic provided that both R's are not hydrogen.

The term "carboxyalkyl" or "alkoxycarbonyl" refers to the groups "—C(O)O-alkyl", "—C(O)O-substituted alkyl", "—C(O)O—cycloalkyl", "—C(O)O-substituted cycloalkyl", "—C(O)O-alkenyl", "—C(O)O-substituted alkenyl", "—C(O)O—alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "cycloalkylene" refers to the diradical derived from cycloalkyl as defined above and is exemplified by 1,1-cyclopropylene, 1,2-cyclobutylene, 1,4-cyclohexylene and the like.

The term "substituted cycloalkylene" refers to the diradical derived from substituted cycloalkyl as defined above.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "cycloalkenylene" refers to the diradical derived from cycloalkenyl as defined above and is exemplified by 1,2-cyclobut-1-enylene, 1,4-cyclohex-2-enylene and the like.

The term "substituted cycloalkenyl" refers to cycloalkenyl groups having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "substituted cycloalkenylene" refers to the diradical derived from substituted cycloalkenyl as defined above.

The term "halo" or "halogen" refers to fluoro, chloro, bromo and iodo.

The term "heteroaryl" refers to an aromatic group comprising 1 to 15 carbon atoms and 1 to 4 heteroatoms selected from oxygen, nitrogen and sulfur within at least one ring.

Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Preferred aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

The term "heteroaryloxy" refers to the group heteroaryl-O—.

The term "heteroarylene" refers to the diradical group derived from heteroaryl (including substituted heteroaryl), as defined above, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, having from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Preferred heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "thioheterocyclooxy" refers to the group heterocyclic-SO—.

The term "heterocyclene" refers to the diradical group formed from a heterocycle, as defined herein, and is exemplified by the groups 2,6-morpholino, 2,5-morpholino and the like.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "spiro-attached cycloalkyl group" refers to a cycloalkyl group attached to another ring via one carbon atom common to both rings.

The term "thiol" refers to the group —SH.

The term "thioalkoxy" refers to the group —SO-alkyl.

The term "substituted thioalkoxy" refers to the group —S-substituted alkyl.

The term "thioaryloxy" refers to the group aryl—S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

The term "carboxyamides" include primary carboxyamides (CONH$_2$), secondary carboxyamides (CONHR') and tertiary carboxyamides (CONR'R"), where R' and R" are the same or different substituent groups chosen from alkyl, alkenyl, alkynyl, alkoxy, aryl, a heterocyclic group, a functional group as defined herein, and the like, which themselves may be substituted or unsubstituted.

"Carboxyamidealkyl" means a carboxyamide as defined above attached to an optionally substituted alkylene group as defined above.

The term "saccharide" includes oxidized, reduced or substituted saccharides, including hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as open chain forms of sugars, and the like. Examples of amine-derivatized sugars are galactosamine, glucosamine, and sialic acid.

The term "site-directing molecule" refers to a molecule having an affinity for a biological receptor or for a nucleic acid sequence. Exemplary site-directing molecules useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins. The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. The alkenyl group is preferably allyl. The alkyl group is preferably a methyl group and the methyl group is attached to the 2' oxygen of the ribose. Other alkyl groups may be ethyl or propyl. It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates, phosphoramidates and the like. Deoxyribonucleotides, deoxyribonucleotide analogs and ribonucleotide analogs are contemplated as site-directing molecules in the present invention. The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing molecule may be attached either directly to the texaphyrin or to the texaphyrin via a linker or a couple of variable length.

The term "catalytic group" means a chemical functional group that assists catalysis by acting as a general acid, Bronsted acid, general base, Bronsted base, nucleophile, or any other means by which the activation barrier to reaction is lowered. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, (LysAla), (LysLeuAla)$_n$ where n is from 1–30 or preferably 1–10 or more preferably 2–7 and the like; derivatives thereof; and metallotexaphyrin complexes.

A "chemotherapeutic agent" may be, but is not limited to, one of the following: an alkylating agent such as a nitrogen mustard, an ethyleneimine or a methylmelamine, an alkyl sulfonate, a nitrosourea, or a triazene; an antimetabolite such as a folic acid analog, a pyrimidine analog, or a purine analog; a natural product such as a vinca alkaloid, an epipodophyllotoxin, an antibiotic, an enzyme, taxane, or a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Chemotherapeutic agents are used in the treatment of cancer and other neoplastic tissue. Preferably, the chemotherapeutic agent is a nitrogen mustard, an epipodophyllotoxin, an antibiotic, or a platinum coordination complex. A more preferred chemotherapeutic agent is bleomycin, doxorubicin, taxol, taxotere, etoposide, 4-OH cyclophosphamide, cisplatin, or platinum coordination complexes analogous to cisplatin. A presently preferred chemotherapeutic agent is doxorubicin, taxol, taxotere, cisplatin, or Pt complexes analogous to cisplatin. Various chemotherapeutic agents, their target diseases, and treatment protocols are presented in, for example, Goodman and Gilman's The Pharmacological Basis of Therapeutics, Ninth Ed., Pergamon Press, Inc., 1990; and Remington: The Science and Practice of Pharmacy, Mack Publishing Co., Easton, Pa., 1995; both of which are incorporated by reference herein.

A site directing molecule, or a group having or catalytic or chemotherapeutic activity, identified above by the symbol Y, may be covalently coupled to any position on a metallotexaphyrin by a covalent bond or by a linker (identified above by the symbol X). The term "linker" as used herein means a group that covalently connects Y to a metallotexaphyrin, and may be, for example, alkylene, alkenylene, alkynylene, arylene, ethers, PEG moieties, and the like, all of which may be optionally substituted. Examples of reactions to form a covalent link include reaction between an amine (on either the molecule Y or X) with a carboxylic acid (on the corresponding X or Y) to form an amide link. Similar reactions well known in the art are described in standard organic chemistry texts such as J. March, "Advanced Organic Chemistry", 4$^{th}$ Edition, (Wiley-Interscience (New York), 1992.

The term "macrocycle" as used herein refers to a class of polypyrrole macrocycles that are capable of forming stable complexes with metals by incorporating a metal (as its cation) within a central binding cavity (core) of the macrocycle, and the anions associated with the metal cation are found above and below the core; these anions are known as apical ligands. This class of macrocycles includes porphyrins, the so-called "expanded porphyrins", and similar structures. Specific examples are porphyrins, porphyrin isomers, porphyrin-like macrocycles, benzophyrins, texaphyrins, alaskaphyrins, sapphyrins, rubyrins, porphycenes, chlorins, benzochlorins, and purpurins.

The term "apical ligand" refers to an anion that binds to the core metal of the MTD with de-localized electrostatic bonds. The number of apical ligands (n) is defined as an integer of 1–5. It should be noted that the apical ligands act to neutralize the charge on the metallotexaphyrin. Thus, typically n is 1 when M is a divalent cation, and n is 2 when M is a trivalent cation (because the core itself neutralizes one unit charge). However, if any of $R^1$, $R^2$, $R^3$, $R^4$, $R^6$, $R^7$, $R^8$, $R^9$, $R^{10}$, $R^{11}$, and $R^{12}$ is capable of forming an acid addition salt, for example a carboxylate or a phosphate, then n will decrease appropriately. It is also possible that the apical ligands could have two functionalities capable of forming an anion, for example a dicarboxylic acid, and such ligands are intended to be within the scope of the invention.

In general, any molecule containing a carboxylic acid or phosphate may be used as an apical ligand, for example biomolecules, including lipoproteins, estradiol and amino acids, carboxylates of sugar derivatives, such as gluconic acid or glucoronic acid, cholesterol derivatives such as cholic acid and deoxycholic acid, PEG acids, organophosphates, such as methylphosphonic acid and phenylphosphonic acid, and phosphoric acid or other inorganic acids, and the like, or sulfonic acid derivatives such as methanesulfonic acid, ethanesulfonic acid or "carboxylic acid derivatives", which term refers to compounds of the formula R—CO$_2$H, in which R is optionally substituted alkyl, optionally substituted alkenyl, optionally substituted alkynyl, or optionally substituted aryl, as defined above. Preferred are gluconic and glucuronic acid, and those carboxylic acid derivatives where R is optionally substituted alkyl, for example acids of 1–20 carbon atoms, such as formic acid, acetic acid, propionic acid, butyric acid, pentanoic acid, 3,6,9-trioxodecanoic acid, 3,6-dioxoheptanoic acid, methylvaleric acid, glycolic acid, pyruvic acid, oxalic acid, malic acid, malonic acid, succinic acid, maleic acid, fumaric acid, tartaric acid, citric acid, and the like. Also preferred are those carboxylic acid derivatives where R is aryl, in particular where R is optionally substituted phenyl, for example benzoic acid, salicylic acid, 3-fluorobenzoic acid, 4-aminobenzoic acid, cinnamic acid, mandelic acid, p-toluene-sulfonic acid, 2-[4-[2-[(3,5-dimethylphenyl)amino]-2-oxoethyl]phenoxy]-2-methyl-propanoic acid, and the like.

It should be noted that the term "apical ligands" as associated with metallotexaphyrins was employed in U.S. Pat. No. 4,935,498, in which the apical ligands were said to include pyridine and benzimidazole, and in U.S. Pat. No. 5,801,229, in which the apical ligands were said to include acetate, chloride, nitrate, hydroxy, water, and methanol. However, pyridine, benzimidazole, water, and methanol are not apical ligands as defined herein, since they are not anions associated with a metal cation; for the purpose of this application, such derivatives are referred to as "coordination complexes."

As to any of the above groups that contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "compound of Formula I" is intended to encompass the metallotexaphyrins of the invention as disclosed, coordination complexes of the compounds of Formula I, and/or the pharmaceutically acceptable salts of such compounds.

The term "therapeutically effective amount" refers to that amount of an MTD of Formula I that is sufficient to effect treatment, as defined below, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose will vary depending on the particular compound of Formula I chosen, the dosing regimen to be followed, timing of administration, the tissue to be imaged, and the physical delivery system in which it is carried.

"Texaphyrin" means an aromatic pentadentate macrocyclic expanded porphyrins, also described as an aromatic benzannulene containing both 18π- and 22π-electron delocalization pathways. Texaphyrins and water-soluble texaphyrins, method of preparation and various uses have been described in U.S. Pat. Nos. 4,935,498, 5,162,509, 5,252,720, 5,256,399, 5,272,142, 5,292,414, 5,369,101, 5,432,171, 5,439,570, 5,451,576, 5,457,183, 5,475,104, 5,504,205, 5,525,325, 5,559,207, 5,565,552, 5,567,687, 5,569,759, 5,580,543, 5,583,220, 5,587,371, 5,587,463, 5,591,422, 5,594,136, 5,595,726, 5,599,923, 5,599,928, 5,601,802, 5,607,924, 5,622,946, and 5,714,328; PCT publications WO 90/10633, 94/29316, 95/10307, 95/21845, 96/09315, 96/40253, 96/38461, 97/26915, 97/35617, 97/46262, and 98/07733; allowed U.S. patent applications Ser. Nos. 08/458,347, 08/591,318, and 08/914,272; and pending U.S. patent application Ser. Nos. 08/763,451, 08/903,099, 08/946,435, 08/975,090, 08/975,522, 08/988,336, and 08/975,526; each of which are herein incorporated by reference in their entirety.

Texaphyrins are illustrated as a compound of Formula I above. Two positions on the compound of Formula I are designated as $R^1$, and two positions are designated as $R^4$. This is because, in general, the disclosed methods of synthesis of texaphyrins leads to the same substituent at $R^1$, and the same substituents at $R^4$. However, it should be noted that methods of synthesis of texaphyrins in which these positions are the same or different are described in U.S. patent application Ser. No. 60/229,247, filed on Aug. 30, 2000, the complete disclosure of which is hereby incorporated by reference in its entirety.

"Sapphyrins" and water-soluble sapphyrins and methods of preparation have been described in U.S. Pat. Nos. 5,041,078; 5,120,411; 5,159,065; 5,302,714; 5,457,195; 5,530,123; 5,543,514; and 5,672,490; and in International Publn. WO 94/09003; all of which are incorporated herein by reference in its entirety.

"Optional" or "optionally" means that the subsequently described event or circumstance may or may not occur, and that the description includes instances where said event or circumstance occurs and instances in which it does not.

"Water soluble" means soluble in an aqueous medium to about 1 mM or more.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "treatment" or "treating" means any treatment of a disease in a mammal, including:
 (i) preventing the disease, that is, causing the clinical symptoms of the disease not to develop;
 (ii) inhibiting the disease, that is, arresting the development of clinical symptoms; and/or
 (iii) relieving the disease, that is, causing the regression of clinical symptoms.

The term "pharmaceutically acceptable salt" refers to salts which retain the biological effectiveness and properties of the MTDs of this invention and which are not biologically or otherwise undesirable. In many cases, the compounds of this invention are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri (cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Specific examples of suitable amines include, by way of example only, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

Nomenclature

The naming and numbering of the MTDs of the present invention is illustrated with a representative compound texaphyrin of Formula I, AL is gluconate (Gluc), and the metal M is lutetium (Lu), depicted below as a compound of Formula IA:

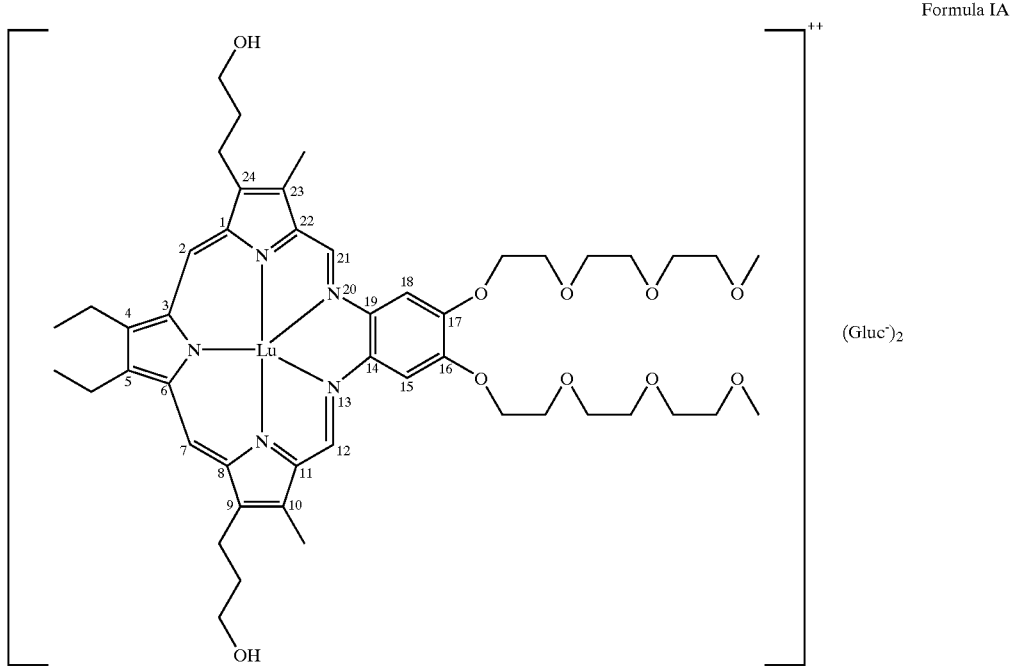

Formula IA

This compound can be named in a variety of ways (e.g. depending on the origination of the numbering). Examples of alternative names for this compound are:

The lutetium (III) complex of: 4,5-diethyl-10,23-dimethyl-9,24-bis(3-hydroxy propyl)-16,17-bis[2-[2-(2 methoxyethoxy)ethoxy]ethoxy]pentaazapentacyclo [20.2.1.1$^{3,6}$.1$^{8,11}$.0$^{14,19}$]heptacosa-1,3,5,7,9,11(27),12,14, 16,18,20,22(25), 23-tridecaene bis gluconate; or Bis (gluconato-O)[9,10-diethyl-20,21-bis[2-[2-(2-methoxy-ethoxy)ethoxy]ethoxy]-4,15-dimethyl-8,11-imino-3,6,16, 13-dinitrilo-1,18-benzodiazacyclooeicosine-5,14-dipropanolato-N$^1$, N$^{18}$, N$^{23}$, N$^{24}$, N$^{25}$]lutetium; or Lutetium texaphyrin bis-gluconate; or Lu-Tex bis-gluconate; or Lu-Tex digluconate.

For the purposes of this specification, the format (Metal)-Macrocycle-Apical Ligand (such as LuTex diacetate or LuTex bisacetate, or LuTex bis-gluconate) is preferred.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, e.g., to bring a solution to the desired volume (i.e., 100%).

Unless specified to the contrary, the reactions described herein take place at atmospheric pressure within a temperature range from 5° C. to 100° C. (preferably from 10° C. to 50° C.; most preferably at about "room" or "ambient" temperature, e.g., about 20° C.).

Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Isolation and purification of the compounds and intermediates described herein can be effected, if desired, by any suitable separation or purification procedure, such as crystallization, distillation, filtration, extraction, column chromatography, solvent evaporation under reduced pressure; thin layer chromatography, thick layer chromatography, preparative low or high pressure liquid chromatography, or a combination of these procedures. Specific illustrations of suitable separation and isolation procedures can be had by reference to the examples hereinbelow. However, other equivalent separation or isolation procedures can, of course, also be used.

Synthesis of the Compounds of Formula I

Alternative syntheses of the compounds of Formula I are described below with reference to Reaction Schemes 1 and 2.

Reaction Scheme 1 illustrates a preferred synthesis of the compounds of Formula I. A texaphyrin with the desired apical ligand(s) (a compound of Formula I) is obtained by an exchange reaction between a metallotexaphyrin having displaceable apical ligands, preferably acetate, and an appropriately charged ion exchange resin. To this end, the desired apical ligand (AL)H is bound to an ion exchange resin, and the ion exchange resin complex thus obtained is reacted with the starting metallotexaphyrin having displaceable apical ligands. The product is separated and purified conventionally.

Reaction Scheme 1

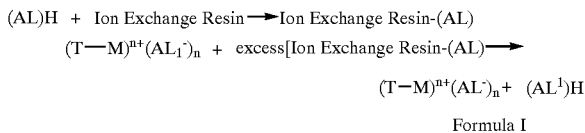

Formula I in which T is a texaphyrin, M is a metal, (AL$_1$) represents the apical ligand associated with the starting texaphyrin, (AL) represents the desired apical ligand that replaces (AL$_1$), n is an integer of 1–5, and the ion exchange resin is a commercially available resin such as Ambersep® 900 (OH) anion exchange resin.

For example, starting with a compound in which T is the texaphyrin illustrated as the compound of Formula IA, as its bis acetate, and reacting with an ion exchange resin prepared with gluconic acid (i.e., (AL)H is gluconic acid), the product obtained is LuTex bis gluconate, a compound of Formula I.

Reaction Scheme 2 illustrates an alternative synthesis of the compounds of Formula I, utilizing an in-situ exchange of apical ligands. A metallotexaphyrin having one or more apical ligands, preferably acetate, is reacted with an excess of the desired apical ligand, optionally at raised temperatures.

Reaction Scheme 2

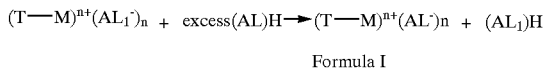

Formula I in which T is a texaphyrin, M is a metal, (AL$_1$) represents the apical ligand associated with M of the starting texaphyrin, (AL) represents the desired apical ligand that replaces (AL$_1$), and n is an integer of 1–5.

For example, starting with a compound in which T is the texaphyrin illustrated as the compound of Formula IA, as its bis acetate, and reacting with an excess of gluconic acid (i.e., (AL)H is gluconic acid), the product obtained is LuTex bis gluconate, a compound of Formula IA. The compound of Formula I is then separated from the mixture conventionally.

Reaction Scheme 3 shows the preparation of a mixture of compounds of Formula.

Reaction Scheme 3

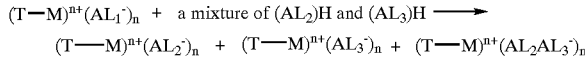

in which T is a texaphyrin, M is a metal, (AL$_1$) represents the apical ligand associated with M of the starting texaphyrin, (AL$_2$) and (AL3) represent a mixture of desired apical ligands that replaces (AL$_1$), and n is an integer of 1–5.

This reaction can be carried out as in Reaction Scheme I (using an ion exchange resin), or as shown in Reaction Scheme 2 (using a large excess of a mixture of the apical ligands). Alternatively, the reaction can be carried out in a biphasic mixture, for example in a methylene chloride/water mixture.

An alternative method of preparing the compounds of the invention is to first prepare a metal-apical ligand M(Al)$_n$, where M, Al, and n are as defined above, and then reacting this metal complex with a texaphyrin, and an oxidizing agent, for example oxygen, to give a metallated texaphyrin of Formula I.

Substituting a metallomacrocycle, as defined above, for a metallotexaphyrin in the above reaction schemes and carrying out the reaction in a similar manner provides metallomacrocycle derivatives having different apical ligands.

Starting Materials

The anion exchange resin is commercially available, e.g., from Rohm and Haas. The desired apical ligands, such as gluconic acid, are likewise commercially available or may be readily prepared by those skilled in the art using commonly employed synthetic methodology.

Preferred Compounds

Preferred are the compounds of Formula I in which M is a divalent or trivalent metal, $R^1$ is hydroxyalkyl (in which alkyl preferably has 1–10 carbon atoms), $R^2$, $R^3$ and $R^4$ are alkyl (preferably of 1–6 carbon atoms), $R^7$ and $R^8$ are substituted alkoxy (in which alkoxy preferably has 1–20 carbon atoms), and n is 1–4. $R^5$, $R^6$, $R^9$, $R^{10}$, $R^{11}$ and $R^{12}$ are hydrogen or alkyl of 1–6 carbon atoms.

More preferred are the compounds of Formula I where M is lutetium or gadolinium, $R^1$ is 2-hyrdoxyethyl or 3-hydroxypropyl, $R^2$, $R^3$ and $R^4$ are methyl or ethyl, $R^7$ and $R^8$ are 2-[2-(2-methoxyethoxy)ethoxy]ethoxy], and n is 2. $R^5$, $R^6$, $R^9$, $R^{10}$, $R^{11}$, and $R^{12}$ are preferably hydrogen or methyl.

Most preferred are the following compounds:

The lutetium (III) complex of: 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{8,11}$.0$^{14,19}$]-heptacosa-1,3,5,7,9,11(27),12,14, 16,18,20,22(25), 23-tridecaene bis gluconate;

The lutetium (III) complex of: 4,5-diethyl-10,23-dimethyl-9,24-bis(3-hydroxypropyl)-16,17-bis[2-[2-(2-methoxyethoxy) ethoxy]ethoxy]pentaazapentacyclo [20.2.1.1$^{3,6}$.1$^{8,11}$.0$^{14,19}$]-heptacosa-1,3,5,7,9,11(27),12,14, 16,18,20,22(25), 23-tridecaene bis glucoronate;

The lutetium (III) complex of: 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{8,11}$.0$^{14,19}$]-heptacosa-1,3,5,7,9,11 (27),12,14, 16,18,20,22(25), 23-tridecaene bis formate;

The lutetium (III complex of: 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{8,11}$.0$^{14,19}$]-heptacosa-1,3,5,7,9,1 (27),12,14, 16,18,20,22(25), 23-tridecaene bis benzoate;

The lutetium (III) complex of: 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{8,11}$.0$^{14,19}$]-heptacosa-1,3,5,7,9,11(27),12,14, 16,18,20,22(25), 23-tridecaene bis methylvalerate;

The lutetium (III) complex of:4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1 $^{3,6}$.1$^{8,11}$.0$^{14,19}$]-heptacosa-1,3,5,7,9,11(27),12,14, 16,18,20,22(25),23-tridecaene bis deoxycholate;

The lutetium (III) complex of: 4,5-diethyl-10,23-dimethyl-9,24-bis(3-hydroxypropyl)-16,17-bis[2-[2-(2-methoxyethoxy) ethoxy]ethoxy]pentaazapentacyclo [20.2.1.1$^{3,6}$.1$^{8,11}$.0$^{14,19}$]-heptacosa-1,3,5,7,9,11(27),12,14, 16,18,20,22(25),23-tridecaene bis 3,6,9-trioxodecanoate;

The lutetium (III) complex of: 4,5-diethyl-10,23-dimethyl-9,24-bis(3-hydroxypropyl)-16,17-bis[2-[2-(2-methoxyethoxy) ethoxy]ethoxy]pentaazapentacyclo [20.2.1.1$^{3,6,8,11}$0.$^{14,19}$]-heptacosa-1,3,5,7,9,1 (27),12,14,16, 18,20,22(25), 23-tridecaene bis 3,6-dioxoheptanoate;

The lutetium (III) complex of: 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{81,1}$.0$^{14,19}$]-heptacosa-1,3,5,7,9,11(27),12,14,16,18,20,22(25), 23-tridecaene methylphosphonate;

The lutetium (III) complex of: 4,5-diethyl-10,23-dimethyl-9,24-bis(3-hydroxypropyl)-16,17-bis[2-[2-(2-methoxyethoxy) ethoxy]ethoxy]pentaazapentacyclo [20.2.1.1$^{3,6}$.1$^{8,11}$.0$^{14,19}$]-heptacosa-1,3,5,7,9,11(27),12,14,16,18,20,22(25), 23-tridecaene phenylphosphonate; and The lutetium (III) complex of: 4,5-diethyl-10,23-dimethyl-9,24-bis(3-hydroxypropyl)-16,17-bis[2-[2-(2-methoxyethoxy) ethoxy] ethoxy]pentaazapentacyclo [20.2.1.1 $^{3,6}$.1$^{8,11}$.0$^{14,19}$]-heptacosa-1,3,5,7,9,11(27),12,14,16,18,20,22(25), 23-tridecaene bis-cholate.

Preferred Processes and Last Steps

The MTDs of the present invention can be prepared according to the following last steps:

1. Contacting a metellotexaphyrin of the formula $(T-M)^{n+}$-$(AL^1)_n$ with an Ion Exchange Resin-(AL) complex, to give $(T-M)^{n+}$-$(AL)_n$, a product of Formula I; in which T is a texaphyrin, M is a divalent or trivalent metal, $(AL^1)$ represents the apical ligand associated with M of the starting texaphyrin, (AL) represents the apical ligand that replaces $(AL^1)$, n is 1 or 2, and the ion exchange resin is a commercially available resin such as Ambersep® 900 (OH) anion exchange resin.
2. Contacting a metallotexaphyrin of the formula $(T-M)^{n+}$-$(AL^1)_n$ with an excess of (AL)H ligand, to give $(T-M)^{n+}$-$(AL)_n$, a product of Formula I.
3. Contacting a metallotexaphyrin of the formula $(T-M)^{n+}$-$(AL^1)_n$ with a mixture of $(AL^2)H$ and $(AL^3)H$ ligands, to give a mixture of $(T-M)^{n+}$-$(AL^2)_n$, $(T-M)^{n+}$-$(AL^3)_n$, and $(T-M)^{n+}$-$(AL^2)(AL^3)$, a mixture of products of Formula I.
4. Contacting a metallotexaphyrin of the formula $(T-M)^{n+}$-$(AL^1)_n$ with a reverse phase chromatography absorption column, contacting the column with a salt of the apical ligand (AL), and eluting with a suitable solvent, for example methanol, to give $(T-M)^{n+}$-$(AL)_n$ a product of Formula I.

Utility, Testing and Administration

General Utility

The MTDs of the present invention are effective in the treatment of conditions known to respond to metallotexaphyrin therapy, including diseases characterized by neoplastic tissue, (e.g. the cancers sarcoma, lymphoma, leukemia, carcinoma, brain metastases, glioma, glioblastoma, cancer of the prostate, melanoma, and the like), cardiovascular diseases (e.g., atherosclerosis, intimal hyperplasia and restenosis) and other activated macrophage-related disorders including autoimmune diseases (e.g., rheumatoid arthritis, Sjogrens, scleroderma, systemic lupus erythematosus, non-specific vasculitis, Kawasaki's disease, psoriasis, Type I diabetes, pemphigus vulgaris, multiple sclerosis), granulomatous diseases (e.g., tuberculosis, sarcoidosis, lymphomatoid granulomatosis, Wegener's granulomatosus), inflammatory diseases (e.g., inflammatory lung diseases such as interstitial pneumonitis and asthma, inflammatory bowel disease such as Crohn's disease, and inflammatory arthritis), in transplant rejection (e.g., in heart/lung transplants) and in ophthalmic diseases that result from undesired neovascularization, in particular age-related macular degeneration.

Testing

Activity testing is conducted as described in those patents and patent applications incorporated by reference above, and in the following references, and by modifications thereof. The MTDs of Formula I have been shown to have various in vitro and in vivo activity. See e.g. Young et al., Methods for Cancer Chemosensitization, and U.S. Pat. No. 5,776, 925.

Determination of the various physicochemical characteristics of each MTD can be performed, and are apparent to one skilled in the art and are detailed in, for example, Pharmaceutical Dosage Forms: Parenteral Medications vol. 1, Marcel Dekker Inc., New York, N.Y., 2$^{nd}$ Edition, 1992. The generally accepted tests performed to determine the MTD's characteristics include, for example: determination of solubility, the partition coefficient, the extinction coefficient, and the solution pH of the MTD.

Pharmaceutical Compositions

The MTDs of Formula I are usually administered in the form of pharmaceutical compositions. This invention therefore provides pharmaceutical compositions that contain, as the active ingredient, one or more of the MTDs of Formula I, or a pharmaceutically acceptable salt AND/or coordination complex thereof, and one or more pharmaceutically acceptable excipients, carriers, including inert solid diluents and fillers, diluents, including sterile aqueous solution and various organic solvents, permeation enhancers, solubilizers and adjuvants. The MTDs may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17$^{th}$ Ed. (1985) and "Modern Pharmaceutics", Marcel Dekker, Inc. 3$^{rd}$ Ed. (G. S. Banker & C. T. Rhodes, Eds.).

Administration

The MTDs of Formula I may be administered in either single or multiple doses by any of the accepted modes of administration of agents having similar utilities, for example as described in those patents and patent applications incorporated by reference above, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer, with parenteral and intra-arterial administration being preferred, and intra-arterial being more preferred.

One preferred mode for administration is parental, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

It has been discovered that texaphyrins have a tendency to aggregate in aqueous solution, which potentially decreases their solubility. Aggregation (self-association) of polypyrrolic macrocyclic compounds, including porphyrins, sapphyrins, texaphyrins, and the like, is a common phenomenon in water solution as the result of strong intermolecular van der Waals attractions between these flat aromatic systems. Aggregation may significantly alter the photochemical characteristics of the macrocycles in solution, which is shown by large spectral changes, decrease in extinction coefficient, etc.

It has been found that addition of a carbohydrate, saccharide, polysaccharide, or polyuronide to the formulation decreases the tendency of the texaphyrin to aggregate, thus increasing the solubility of the texaphyrin in aqueous media. Preferred anti-aggregation agents are sugars, in particular mannitol, dextrose or glucose, preferably mannitol of about 2–8% concentration, more preferably about 5% concentration. These aqueous solutions are especially suitable for intravenous, intramuscular, subcutaneous and intraperitoneal administration. In this connection, the sterile aqueous media that can be employed will be known to those of skill in the art in light of the present disclosure.

Prolonged absorption of the injectable compositions can be brought about by the use in the compositions of agents delaying absorption, for example, aluminum monostearate and gelatin. These particular aqueous solutions are especially suitable for intra-arterial, intravenous, intramuscular, subcutaneous and intraperitoneal administration. In this connection, sterile aqueous media that can be employed will be known to those skilled in the art in light of the present disclosure.

Sterile injectable solutions are prepared by incorporating the active MTDs in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

MTDs of Formula I may be impregnated into a stent by diffusion, for example, or coated onto the stent such as in a gel form, for example, using procedures known to one of skill in the art in light of the present disclosure.

Oral administration is another route for administration of the MTDs of this invention. Preferred is oral administration via capsule or enteric coated tablets, or the like, which prevent degradation of the MTDs of the invention in the stomach. In making the pharmaceutical compositions that include at least one MTD of Formula I, the active ingredient is usually diluted by an excipient and/or enclosed within such a carrier that can be in the form of a capsule, sachet, paper or other container. When the excipient serves as a diluent, in can be a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another preferred formulation for use in the methods of the present invention employs transdermal delivery devices ("patches"). Such transdermal patches may be used to provide continuous or discontinuous infusion of the MTDs of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The active MTD is effective over a wide dosage range and is generally administered in a pharmaceutically effective amount. Preferably, for oral administration, each dosage unit contains from 10 mg to 2 g of an MTD of Formula I, and for parenteral administration, preferably from 10 to 700 mg of an MTD of Formula I, preferably about 350 mg. It will be understood, however, that the amount of the MTD actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of an MTD of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

The MTDs disclosed herein can be used both diagnostically (e.g. magnetic resonance or fluorescence imaging to detect the presence of a disease) and therapeutically (to treat that disease).

Activation Means

The compounds of the invention to be used will be administered in a therapeutically effective amount, employing a method of administration and a pharmaceutical formulation as discussed above, and optionally a means of activation of the compound (through a therapeutic energy or agent) as is known in the art. The therapeutic energy or agent to be used includes photodynamic therapy, radiation sensitization, chemotherapy, sonodynamic therapy, and neutron bombardment. The specific dose will vary depending on the particular compound of Formula I chosen, the dosing regimen to be followed, and the particular therapeutic energy or agent with which it is administered. Such dose can be determined by methods known in the art or as described herein.

Dosages: The specific dose will vary depending on the particular compound of Formula I chosen, the dosing regimen to be followed, and the particular therapeutic energy or agent with which it is administered, employing dosages within the range of about 0.01 mg/kg/treatment up to about 100 mg/kg/treatment, preferably about 0.1 mg/kg/treatment to about 50 mg/kg/treatment. It will be appreciated by one skilled in the art, however, that there are specific differences in the most effective dosimetry depending on the apical ligands chosen, because of the wide range of properties available, such as solubilities, lipophilicity properties, lower toxicity, and improved stability.

Administration for Photodynamic Therapy

By way of example, lutetium texaphyrin may be administered in solution, optionally in 5% mannitol USP. Dosages of about 1.0–2.0 mg/kg to about 4.0–7.0 mg/kg, preferably 3.0 mg/kg, are employed, although in some cases a maximum tolerated dose may be higher, for example about 5 mg/kg. The texaphyrin is administered by intravenous injection, followed by a waiting period of from as short a time as several minutes or about 3 hours to as long as about 72 or 96 hours (depending on the treatment being effected) to facilitate intracellular uptake and clearance from the plasma and extracellular matrix prior to the administration of photoirradiation.

Dose levels for certain uses may range from about 0.05 mg/kg to about 20 mg/kg administered in single or multiple doses (e.g. before each fraction of radiation). The lower dosage range would be preferred for intra-arterial injection or for impregnated stents.

The co-administration of a sedative (e.g., benzodiazapenes) and narcotics/analgesics are sometimes recommended prior to light treatment along with topical administration of a local anesthetic, for example Emla cream (lidocaine, 2.5% and prilocaine, 2.5%) under an occlusive dressing. Other intradermal, subcutaneous and topical anesthetics may also be employed as necessary to reduce discomfort. Subsequent treatments can be provided after approximately 21 days.

The optimum length of time following administration of an MTD of Formula I until light treatment can vary depending on the mode of administration, the form of administration, and the type of target tissue. Typically, the MTD of Formula I persists for a period of minutes to hours, depending on the compound of Formula I, the formulation, the dose, the infusion rate, as well as the type of tissue and tissue size.

When employing photodynamic therapy, a target area is treated with light at about 732±16.5 nm (full width at half max) delivered by an LED device or an equivalent light source (e.g., a Quantum Device Qbeam™ BMEDXM-728 Solid State Lighting System, which operates at 728 nm) at an intensity of 5–150 mW/cm$^2$ for a total light dose of 0.5–600 J/cm$^2$, or a solid state diode laser, such as the DioMed 6 WW, 15 W laser).

After the photosensitizing MTD of Formula I has been administered, the tissue being treated is photoirradiated at a wavelength similar to the absorbance of the compound of Formula I, usually either about 400–500 nm or about 700–800 nm, more preferably about 450–500 nm or about 710–760 nm, or most preferably about 450–500 nm or about 725–740 nm. The light source may be a laser, a light-emitting diode, or filtered light from, for example, a xenon lamp; and the light may be administered topically, endoscopically, or interstitially (via, e.g., a fiber optic probe), or intraarterially. Preferably, the light is administered using a slit-lamp delivery system. The fluence and irradiance during the photoirradiating treatment can vary depending on type of tissue, depth of target tissue, and the amount of overlying fluid or blood. For example, a total light energy of about 100 J/cm$^2$ can be delivered at a power of 200 mW to 250 mW, depending upon the target tissue.

Administration for Chemosensitization

MTDs of Formula I may be administered before, at the same time, or after administration of one or more chemotherapeutic drugs. The MTD of Formula I may be administered as a single dose, or it may be administered as two or more doses separated by an interval of time. The MTD of Formula I may be administered concurrently with, or from about one minute to about 12 hours following, administration of a chemotherapeutic drug, preferably from about 5 min to about 5 hr, more preferably about 4 to 5 hr. The dosing protocol may be repeated, from one to three times, for example. A time frame that has been successful in vivo is administration of an MTD of Formula I about 5 min and about 5 hr after administration of a chemotherapeutic agent, with the protocol being performed once per week for three weeks. Administration may be intra-arterial injection, intravenous, intraperitoneal, intramuscular, subcutaneous, oral, topical, or via a device such as a stent, for example, with parenteral and intra-arterial administration being preferred, and intra-arterial being more preferred.

Administering an MTD of Formula I and a chemotherapeutic drug to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of an MTD of Formula I and chemotherapeutic drug will be within 6–12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Radiation Sensitization

MTDs of Formula I where the metal is gadolinium are typically administered in a solution containing 2 mM optionally in 5% mannitol USP/water (sterile and non-pyrogenic solution). Dosages of 0.1 mg/kg up to as high as about 29.0 mg/kg have been delivered, preferably about 3.0 to about 15.0 mg/kg (for volume of about 90 to 450 mL) may be employed, optionally with pre-medication using antiemetics when dosing above about 6.0 mg/kg. The MTD is administered via intravenous injection over about a 5 to 10 minute period, followed by a waiting period of about 2 to 5 hours to facilitate intracellular uptake and clearance from the plasma and extracellular matrix prior to the administration of radiation.

When employing whole brain radiation therapy, a course of 30 Gy in ten (10) fractions of radiation may be administered over consecutive days excluding weekends and holidays. In the treatment of brain metastases, whole brain megavolt radiation therapy is delivered with $^{60}$Co teletherapy or a $\geq 4$ MV linear accelerator with isocenter distances of at least 80 cm, using isocentric techniques, opposed lateral fields and exclusion of the eyes. A minimum dose rate at the midplane in the brain on the central axis is about 0.5 Gy/minute.

MTDs of Formula I used as radiation sensitizers may be administered before, or at the same time as, or after administration of the ionizing radiation. The MTD of Formula I may be administered as a single dose, as an infusion, or it may be administered as two or more doses separated by an interval of time. Where the MTD of Formula I is administered as two or more doses, the time interval between the MTD of Formula I administrations may be from about one minute to a number of days, preferably from about 5 min to about 1 day, more preferably about 4 to 5 hr. The dosing protocol may be repeated, from one to ten or more times, for example. Dose levels for radiation sensitization may range from about 0.05 mg/kg to about 20 mg/kg administered in single or multiple doses (e.g. before each fraction of radiation). The lower dosage range would be preferred for intra-arterial injection or for impregnated stents.

Administration may be intra-arterial injection, intravenous, intraperitoneal, intramuscular, subcutaneous, oral, topical, or via an impregnated or coated device such as a stent, for example, or an artery-inserted cylindrical polymer, with intravenous and intra-arterial administration being preferred, and intra-arterial being more preferred. In one aspect of the invention, a patient having restenosis or at risk for restenosis is administered a dose of MTD of Formula I at intervals with each dose of radiation.

Administering a MTD of Formula I to the subject may be prior to, concurrent with, or following vascular intervention, and the intervention is followed by radiation. The method may begin prior to, such as about 24–48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of MTD of Formula I and radiation will be within 1–24 hours of the vascular intervention, preferably within about 5–24 hours thereafter. Follow-up dosages may be made at weekly, biweekly, or monthly intervals. Design of particular protocols depends on the individual subject, the condition of the subject, the design of dosage levels, and the judgment of the attending practitioner.

Administration for Sonodynamic Therapy:

The use of texaphyrins in sonodynamic therapy is described in U.S. patent application Ser. No. 09/111,148, which is incorporated herein by reference. Texaphyrin is administered before administration of the ultrasound. The texaphyrin may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of the invention. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave.

Preferred types of ultrasound employed in the present invention are ultrasound of low intensity, non-thermal ultrasound, i.e., ultrasound generated within the wavelengths of about 0.1 MHz and 5.0 MHz and at intensities between about 3.0 and 5.0 W/cm$^2$.

Administration for Neutron Capture Therapy

The use of metallotexaphyrins in neutron capture therapy is described in U.S. patent application Ser. No. 60/229,366, entitled "Agents for Neutron Capture Therapy", filed on Aug. 30, 2000, which is incorporated herein in its entirety by reference. The metallotexaphyrin is administered before administration of the neutron beam. It may be administered as a single dose, or it may be administered as two or more doses separated by an interval of time. Parenteral administration is typical, including by intravenous and interarterial injection. Other common routes of administration can also be employed.

Further Administration Protocols

MTDs of Formula I and a suitable co-therapeutic agent can also be administered in the context of other medical procedures. For example, in allograft transplantation administration may be accomplished by perfusion of the graft prior to implantation. Following a brief period for uptake, e.g., by macrophages, the remaining MTD of Formula I is rinsed from the graft followed by application of the co-therapeutic agent. Administration to selectively treat diseases characterized by circulating macrophages may be accomplished by extracorporeal contact, filtration of non-absorbed MTD of Formula I employing a lipophilic filter, followed by application of the co-therapeutic agent.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of Compounds of Formula (I) using an Anion Exchange Resin

A. Preparation of a Compound of Formula I where M is Lutetium, AL is gluconate, and n is 2

Ambersep® 900 (OH) anion exchange resin (100 mL, 90 meq) was slurried in 200 mL of deionized water, poured into a Biorad® column and washed with 500 mL of deionized water until the pH of the eluant was approximately 7. The resin was poured out of the column into an Erlenmeyer flask and the excess solvent decanted.

80 g of gluconic acid were dissolved in 200 mL of deionized water. 100 mL of the aqueous solution were added to the flask and stirred for one hour. The resultant mixture was poured onto the Biorad column and the excess solution drained. The remaining 150 mL of gluconic acid solution was then passed through the column followed by 500 mL of water (until the pH $\mu$4) and methanol (500 mL).

LuTex diacetate (1.1687 g, 1.002 mmol) was dissolved in 50 mL of methanol and passed through the Biorad column. The column was washed with 25 mL of methanol. The collected eluant was passed through the column a second time and the column was washed with an additional 100 mL of methanol. The combined solutions from the column were collected and the methanol was evaporated under reduced pressure. The green solid was dried overnight under vacuum to afford the lutetium complex of 4,5-diethyl-10,23-dimethyl-9,24-bis(3-hydroxypropyl)-16,17-bis[2-[2-(2-methoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis gluconate. (Alternatively, LuTex bis gluconate). Characterizing analytical data are m.w.=1438.33; g (methanol) 42200 (at 733 mm), 127900 (at 475 nm); K (octanol/water) 0.011 (0.5 mg/ml), 0.028 (0.05 mg/ml); pH=5.6 (H$_2$O); pH$_{(octanol/water)}$=5.1 (0.5 mg/ml), 5.7 (0.05 mg/ml).

B. Preparation of other Compounds of Formula I where M is Lutetium, and n is 2, varying AL Similarly, following the procedure of Example IA above, substituting other ligands for gluconic acid, the following compounds of Formula IA were prepared:

1) Substituting glucoronic acid for gluconic acid gave the lutetium complex of:
   4,5-diethyl-10,23-dimethyl-9,24-bis(3-hydroxypropyl)-16,17-bis[2-[2-(2-methoxyethoxy)ethoxy]ethoxy]pentaazapentacyclo[20.2.1.1$^{3,6}$.1$^{8,11}$.0$^{14,19}$]heptacosa-1,3,5,7,9,11(27),12,14,16,18,20,22(25), 23-tridecaene bis glucoronate (LuTex bis glucuronate); (0.885 mmol, 98.2% yield);

2) Substituting formic acid for gluconic acid gave the lutetium complex of:4,5-diethyl-10,23-dimethyl-9,24-bis(3-hydroxypropyl)-16,17-bis[2-[2-(2-methoxy-ethoxy)ethoxy]ethoxy]-pentaazapenta-cyclo[20.2.1.1.1$^{3,6}$.1$^{8,11}$.0$^{14,19}$]heptacosa-1,3,5,7,9,11(27),12,14,16–18, 20,22(25), 23-tridecaene bis formate. (LuTex bis formate) (0.885 mmol, 98.2% yield); Characterizing analytical data are m.w. 1138.07; $\epsilon$(methanol)=41700 (at 733 nm), 126400 (at 475 nm); K(octanol/water)=0.02 (0.5 mg/ml), 0.02 (0.05 mg/ml); pH=5.5 (H$_2$O); pH(octanol/water)=5.1 (0.5 mg/ml), 5.6 (0.05 mg/ml).

3) Substituting benzoic acid for gluconic acid gave the lutetium complex of:4,5-diethyl-10,23-dimethyl-9,24-bis(3-hydroxypropyl)-16,17-bis[2-[2-(2 methoxyethoxy)ethoxy]-ethoxy]pentaazapentacyclo[20.2.1.1 $^{3,6}$.1$^{8,11}$.0$^{14,19}$]heptacosal,3,5,7,9,11(27),12,14,16,18,20,22-(25), 23-tridecaene bis benzoate. (LuTex bis benzoate) (0.885 mmol, 98.2% yield); Characterizing analytical data are m.w.=1290.26; $\epsilon$(methanol)=40600 (at 733 nm), 122800 (at 475 nm); K (octanol/water)=0.34 (0.05 mg/ml); pH=6.1 (H$_2$O); pH$_{(octanol/water)}$=6.6 (0.05 mg/ml).

4) Substituting methylvaleric acid for gluconic acid gave the lutetium complex of:4,5-diethyl-10,23-dimethyl-9,24-bis(3-hydroxypropyl)-16,17-bis[2-[2-(2-methoxyethoxy)ethoxy]-ethoxy]pentaazapentacyclo[20.2.1.1$^{3,6}$.1$^{8,11}$.0$^{14,19}$]heptacosa1,3,5,7,9,11(27), 12,14,16,18,2, 0,22(25), 23-tridecaene bis methyl valerate (LuTex bis methylvalerate).

5) Substituting deoxycholic acid for gluconic acid gave the lutetium complex of:4,5-diethyl-10,23-dimethyl-9,24-bis(3-hydroxypropyl)-16,17-bis[2-[2-(2-methoxyethoxy)ethoxy]-ethoxy]pentaaza-pentacyclo[20.2.1.1 $^{3,6}$.1$^{8,11}$.0$^{14,19}$]heptacosa1,3,5,7,9,11(27),12,14,16,18,20-,22 (25), 23-tridecaene bis deoxycholate (LuTex bis deoxycholate). Characterizing analytical data are m.w.=1831.2; $\epsilon$(methanol)=136000; $\epsilon$(4% acetate/methanol)=135000; K=2.62; pH=6.11.

6) Similarly, substituting:
   a) 3,6,9-trioxodecanoic acid;
   b) 3,6-dioxoheptanoic acid;
   c) methylphosphonic acid;
   d) phenylphosphonic acid;
   e) cholic acid; and
   f) 2,5 dioxoheptanoate;
for gluconic acid, the following lutetium complexes of Formula IA were obtained, respectively;
   a) 4,5-diethyl-10,23-dimethyl-9,24-bis(3-hydroxypropyl)-16,17-bis[2-[2-(2-methoxyethoxy)ethoxy]pentaazapentacyclo[20.2.1.1 $^{3,1^6}$.1$^{8,11}$.0$^{14,19}$]heptacosa-1,3,5,7,9,11 (27),12,14,16,18, 20,22(25), 23-tridecaene bis 3,6,9-trioxodecanote;
   b) 4,5-diethyl-10,23-dimethyl-9,24-bis(3-hydroxypropyl)-16,17-bis[2-[2-(2-methoxyethoxy)-ethoxy]ethoxy]pentaazapentacyclo[20.2.1.1$^{3,6}$.1$^{8,11}$.0$^{14,19}$]heptacosa-1,3,5,7,9,11(27),12,14,16,18,20,22(25), 23-tridecaene bis 3,6-dioxoheptanoate;
   c) 4,5-diethyl-10,23-dimethyl-9,24-bis(3-hydroxypropyl)-16,17-bis[2-[2-(2-methoxyethoxy)ethoxy]ethoxy]pentaazapentacyclo[20.2.1. 1$^{3,6}$.1$^{1.811}$0.$^{14,19}$] heptacosa-1,3,5,7,9,11(27),12,14,16, 18,20,22(25), 23-tridecaene methylphosphonate;
   d) 4,5-diethyl-10,23-dimethyl-9,24-bis(3-hydroxypropyl)-16,17-bis[2-[2-(2-methoxyethoxy)ethoxy]ethoxy]pentaazapentacyclo[20.2.1.1$^{3,6}$.1$^{8,11}$.0$^{14,19}$]heptacosa-1,3,5,7,9,11(27),12,14,16,18,20, 22(25), 23-tridecaene phenylphosphonate; and
   e) 4,5-diethyl-10,23-dimethyl-9,24-bis(3-hydroxypropyl)-16,17-bis[2-[2-(2-methoxyethoxy)

ethoxy]ethoxy]pentaazapentacyclo[20.2.1.1$^{3,6}$.1$^{8,11}$.0$^{14,19}$]heptacosa-1,3,5,7,9,11(27),12,14,16,18,20,22(25), 23-tridecaene bis-cholate.

f) 4,5-diethyl-10,23-dimethyl-9,24-bis(3-hydroxypropyl)-16,17-bis[2-[2-(2-methoxyethoxy)ethoxy]ethoxy]pentaazapentacyclo[20.2.1.1$^{3,6}$.1$^{8,11}$.0$^{14,19}$]heptacosa-1,3,5,7,9,11(27),12,14,16,18,20,22(25), 23-tridecaene bis 2,5 dioxoheptanoate.

C. Preparation of other Compounds of Formula I

Similarly, following the procedure of Example IA above, optionally substituting other apical ligands for gluconic acid, and optionally substituting other metallotexaphyrins for LuTex diacetate, the following compounds of Formula IA are prepared:

gadolinium (III) complex of 4,5-diethyl-10,23-dimethyl-9,24-bis(3-hydroxypropyl)-16,17-bis[2-[2-(2-methoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis gluconate;

manganese (III) complex of 4,5-diethyl-10,23-dimethyl-9,24-bis(3-hydroxypropyl)-16,17-bis[2-[2-(2-methoxyethoxy)ethoxy]ethoxy]pentaazapentacyclo-[20.2.1.1.$^{3,6}$.1$^{8,11}$.0$^{14,19}$]heptacosa-1,3,5,7,9,11(27),12,14,16,18,20,22,(25), 23-tridecaene bis glucuronate;

yttrium (III) complex of 4,5-diethyl-10,23-dimethyl-9,24-bis(3-hydroxypropyl)-16,17-bis[2-[2-(2-methoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis methylvalerate;

lutetium (III) complex of 4,5-dimethyl-10,23-diethyl-9,24-bis(2-hydroxyethyl)-16,17-bis[2-[2-(2-hydroxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis gluconate;

gadolinium (III) complex of 4,5-dimethyl-10,23-diethyl-9,24-bis(2-hydroxyethyl)-16,17-bis[2-[2-(2-hydroxyethoxy)ethoxy] ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis cholate;

lutetium (III) complex of 4-methyl-5-ethyl-10,23-diethyl-9,24-bis(2-hydroxybutyl)-16,17-bis[2-[2-(2-hydroxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis formate;

calcium (II) complex of 4,5-diethyl-10,23-dimethyl-9,24-bis(3-hydroxypropyl)-16,17-bis[2-[2-(2-methoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene gluconate;

lutetium (III) complex of 4,5-difluoro-10,23-dimethyl-9,24-bis(2-hydroxyethyl)-16,17-bis[2-[2-(2-hydroxyethoxy)ethoxy]ethoxy]pentaazapentacyclo-[20.1.1$^{3,6}$.1$^{8,11}$0.$^{14,19}$]heptacosa-1,3,5,7,9,11(27),12,14,16,18,20,22(25), 23-tridecaene bis gluconate;

lutetium (III) complex of 4-phenyl-5-ethyl-10,23-diethyl-9,24-bis(2-hydroxyethyl)-16,17-bis[2-[2-(2-ethoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis gluconate;

lutetium (III) complex of 4,5-dimethyl-10,23-diethyl-9,24-bis(2,3-dihydroxypropyl)-16,17-bis[2-[2-(2-methoxyethoxy)ethoxy]ethoxy]pentaazapentacyclo-[20.2.1.1$^{3,6,1}$.1$^{8,11}$.0$^{14,19}$]heptacosa-1,3,5,7,9,11(27),12,14,16,18,20,22(25), bis gluconate;

lutetium (III) complex of 4,5-dihydroxy-10,23-diethyl-9,24-bis(2-hydroxyethyl)-16,17-bis [2-[2-(2-hydroxyethoxy)ethoxy]ethoxy]pentaazapentacyclo-[20.2.1.1$^{3,6}$.1$^{8,11}$.0$^{14,19}$]heptacosa-1,3,5,7,9,11,(27),12,14,16,18,20,22(25), 23-tridecaene bis glucuronate; and lutetium (III) complex of 4,5-bis(dimethylamino)-10,23-diethyl-9,24-bis(2-hydroxyethyl)-16,17-bis[2-[2-(2-ethoxyethoxy)ethoxy]ethoxy]pentaazapentacyclo-[20.2.1.1$^{3,6}$.1$^{8,11}$.0$^{14,\,19}$]heptacosa-1,3,5,7,9,11(27),12,14,16,18,20,22(25), 23-tridecaene bis gluconate.

Example 2

Preparation of Metallotexaphyrins via Solution Phase Extraction

The metallotexaphyrin complex (200 μmol) is dissolved in 200 ml of deionized water. 400–600 mmol of the conjugate base of the apical ligand is added, causing the precipitation of the metallotexaphyrin. Dichloromethane (200 ml) is added, and the biphasic mixture allowed to stir vigorously for several hours. The solutions are allowed to separate and the organic layer collected. The aqueous layer is extracted twice with dichloromethane (50 ml) and the combined organics evaporated under reduced pressure and dried overnight in vacuo.

Example 3

Preparation of LuTex bis Phospate via Reaction Scheme 2

1.11 g of Lu-Tex diacetate (10 mg/ml) was dissolved in 20 mM of phosphate (with 4% mannitol buffer) in a 150 ml beaker and stirred. The resultant mixture was poured through a Nalgene® filter, equipped with a 0.2 μm Nylon® membrane to afford 10.4 mg/ml 4,5-diethyl-10,23-dimethyl-9,24-bis(3-hydroxypropyl)-16,17-bis[2-[2-(2 methoxyethoxy)ethoxy]ethoxy]-pentaazapentacyclo [20.2.1.1$^{3,6}$.1$^{8,11}$.0$^{14,19}$]heptacosa-1,3,5,7,9,11(27),12,14,16,18,20,22(25), 23-tridecaene bis phospate (LuTex bis phosphate) in an acetate buffer.

Example 4

Determination of In vitro Characteristics of the Compounds of Formula I

4A. Extinction Coefficient

Four samples of increasing amounts of a test compound of Formula I (between 3 mg and 11 mg) were put into separate 10 ml flasks and dissolved in methanol. Each of the solutions and one control sample (containing no test compound) were diluted to volume. The absorption at 475 nm was measured by UV/V is and recorded for each of the five samples. The extinction coefficient for each sample was determined accordingly.

Extinction Coefficient (ε)=Absorption at 475 nm)(M.W. of test compound/amount of test compound mg/volume: 100 ml The extinction coefficient for the test compound at 475 nm was determined by averaging the extinction coefficient for the four samples (not including the control). The above steps were repeated (at 733 nm) to determine the extinction coefficient for the test compound at 733 nm. When determining the extinction coefficient of aggregated test compounds LuTex acetate, cholate or deoxycholate, the extinction coefficient at 733 nm is not measured. Instead, the above steps were repeated substituting 4% acetic acid/methanol for methanol.

4B. Solubility in $H_2O$

The test compound of Formula I was added to 10 ml of deionized water in increasing mass until some of the test compound was visibly observed not to dissolve. This mixture was then shaken, and 1.5 ml of the supernatant removed by a syringe equipped with a 0.22 μm filter unit. After discarding the first 1 mL of the filtrate, the remaining 0.5 mL was collected and saved. 0.1 ml of the saved filtrate was added to a 25 ml flask and diluted with 4% Acetic Acid/Methanol solution to volume. The absorption of the diluted solution at 475 nm was measured by UV/V is at 1, 4, and 24 hours after the solutions had been shaken as described above. The concentration of the compound was determined by the formula:

$$[\text{Concentration}] \text{ mg/ml} = \frac{\text{Absorption at 475 nm} \times \text{Molecular Weight}}{\text{Extinction Coefficient}}$$

The solubility of the test compound is determined by referencing the concentration with the descriptive solubility term set forth in a table in U.S. Pharmacopeia The National Formulary, United States Pharmacopeial Convention, Inc., Rockville, Md., 1997.

4C. pH

The test compound was mixed in 5 ml of deionized water to achieve a 2 mg/ml solution. The solution pH was measured using a Beckman pH meter.

4D. Partition Coefficient

The partition coefficient was measured using an adaptation of the procedure outlined in Drug Stability: Principles and Practices (AAI, Inc. Wilmington, N.C. $2^{nd}$ Edition, 1995). A 10 ml solution of 10 mg/ml of the test compound of Formula I dissolved in deionized water was placed in a separator funnel, to which 10 ml of 1-octanol was added. The combined mixture was stirred. The mixture was left to separate and the absorption of the compound was measured in the water phase and in the octanol phase by UV/V is at 413–417 nm (413–417 offers the closest match in absorbance between the octanol phase and the water phase. The octanol water partition coefficient is determined by the formula:

$$K = \frac{\frac{(\text{Absorption of octanol phase at 413-417 nm})}{(\text{dilution of octanol})}}{\frac{(\text{Absorption of water phase at 413-417 nm})}{(\text{dilution of water})}}$$

The above steps were then repeated using a 10 ml sample of test compound at 1.0 mg/ml.

4E. Representative Compounds of The Invention

When tested in accordance with the procedures of Examples 4A through 4D, the characteristic data for the following representative compounds of the invention was determined:

Lutetium Texaphyrin Diacetate, Lutetium Texaphyrin Bis-Gluconate, Lutetium Texaphyrin Bis-Formate, Lutetium Texaphyrin Bis-Benzoate, Lutetium Texaphyrin Bis-Cholate, and Lutetium Texaphyrin Bis-Deoxycholate For example, the solubility of representative compounds of Formula I was determined in deionized water as follows (LuTex diacetate shown for comparison):

| Lutetium Texaphyrin Diacetate | Lutetium Texaphyrin Bis-Gluconate | Lutetium Texaphyrin Bis-Formate | Lutetium Texaphyrin Bis-Benzoate | Lutetium Texaphyrin Bis-Cholate | Lutetium Texaphyrin Bis-Deoxycholate |
|---|---|---|---|---|---|
| 2.4 mg/ml | 50–80 mg/ml | 2–2.5 mg/ml | 0.1 mg/ml | 5.0 mg/ml | 5.5 mg/ml |

Example 5

In Vivo Studies

5A. Biodistribution in Plaque

Plasma pK and biodistribution of the different test compounds of Formula I in plaque are determined and compared with the plasma pK and biodistribution in normal arterial walls. Sixteen normal male NZW rabbits, each weighing 3.5–4.0 kg are obtained from R&R Rabbitry in Stanwood Oreg. Each rabbit is given an intramuscular injection of Ketamine/Rompun [(8.4 mg/kg)/(1.2 mg/kg)] and allowed to relax until the anesthetic takes effect. To induce deep anesthesia, the rabbits then receive a second dose of Ketamine/Rompun [(8.4 mg/kg)/1.2 mg/kg)] via intravenous injection. To expose the abdomen and back legs, each rabbit is shaved with a size 40 blade. Their eyes are coated with lubricant eye ointment (Artificial Tears).

A femoral artery cut down is performed on the right side of the rabbits. Lidocaine (2%) is injected subcutaneously around the femoral artery as a local anesthetic and also applied topically to prevent spasms. A No.4 French Fogarty balloon embolectomy catheter is inserted retrograde 15 cm into the abdominal aorta. The balloon is inflated with 0.5–0.75 ml of hypaque contrast and pulled 3.5 cm distally toward the femoral artery six times. The catheter is then withdrawn. The incision line on the underlying muscle is sutured with 3-0 absorbable chromic gut (Ethicon) and the skin is sutured with 2-0 silk (Ethicon). The rabbits are allowed to recover before being placed back into their respective cages and are placed on a 2% cholesterol diet for 6–8 weeks.

A 3 ml blood sample is taken from each of the rabbits and the cholesterol level for each sample is determined and recorded. Fourteen of the sixteen rabbits are injected with 10 mg/kg of one of the test compounds. One of the remaining rabbits is a pure control and receives neither test compound nor buffer. The other remaining rabbit receives no test compound but does receive 5% mannitol buffer. A 3 ml blood sample is drawn from each of the rabbits at 1, 5 and 24 hours post injection. Each 3 ml blood sample is handled with minimum exposure to ambient light and spun for 10 minutes in a centrifuge at 2,000 rpm within 30 minutes of the blood draw. The supernatant (plasma) is removed by a pipette and put into a 1.8 ml cryotube. The plasma is frozen at −70° C. for future analysis (see part B of this example). All of the rabbits are sacrificed 24 hours after injection.

At necropsy, the heart and aorta, including the iliac arteries, are harvested in a minimum amount of ambient light. The length of the plaque (cm) in the aorta is measured. The iliac arteries and lower abdominal aortic sections of the above rabbits were subjected to fluorescence spectral bioimaging. Each aorta is excised, cut longitudinally to expose the luminal surface and washed thoroughly with isotonic saline. The luminal surfaces of the iliac arteries and the lower abdominal aorta were compared to the surrounding visually normal aortic surfaces. The aortic samples were illuminated with a Cogent Light illumination system equipped with a coaxial LightWear headlight (Cogent Light Technologies, Inc., Santa Clara, Calif.) and a 470 nm interference filter (10 nm bandwidth, Oriel Corporation, Stratford, Conn.). Images were collected with the SD200 spectral bio-imaging system (Applied Spectral Imaging, Carlsbad, Calif.). A 715 nm long pass filter is utilized (Oriel Corporation, Stratford, Conn.) with a fluorescence emission range of 650–850 nm being captured. Each signal is averaged over 5 pixels. Each acquired measurement is imaged with a CCD camera coupled to an interferometer, and then the signal Fourier transformed allowing spectral identification at every pixel as described by Garini et al., Spectral Bioimaging, John Wiley and Sons, Inc. New York. 1996; 87–124). The results of the fluorescence signal measurements in plaque vs. normal tissue are plotted.

5B. Plasma Concentration

The clearance rate of the test compound is also particularly important to measure. Plasma samples from each of the test compounds (see part A of this example) are mixed with 10 mM Triton X-100 and the fluorescence optimum is measured at 745 nm by scanning between 700–800 nm using a 450 nm excitation. A standard curve is run to insure that the fluorescence of the samples lies on the linear portion of the curve. The entire fluorescence emission spectrum is observed by using both a monochromator and CCD array. This permits differentiating between the peak at 745 nm and any possible extraneous fluorescence that might have a different optimum, and tail off into the 745 nm region. Test compound accumulation is expressed as $\mu$g drug/g tissue (wet weight) or $\mu$g/ml in plasma.

Results

| | Plasma Concentration in $\mu$g/ml | | |
|---|---|---|---|
| | 1 Hour | 5 Hours | 24 Hours |
| 2 mg/ml bisformate | 3.9 | 0.5 | 0.3 |
| 2 mg/ml bisgluconate | 5.6 | 1.5 | 0.4 |
| 10 mg/ml bisgluconate | 2.4 | 0.7 | 0.3 |
| 10 mg/ml bisacetate | 4.5 | 0.8 | 0.3 |
| 2 mg/ml bisacetate | 2.1 | 0.3 | 0.2 |

The numbers of rabbits that are treated with each test compound in parts A and B of this example are set forth in the table below.

| Test compound | Number of Rabbits Injected |
|---|---|
| None (control) | 1 |
| 20 ml of 5% mannitol | 1 |
| 20 ml of LuTex diacetate in 2 g of 5% mannitol | 3 |
| 20 ml of LuTex bis-gluconate in 2 g of 5% mannitol | 3 |
| 2 ml of LuTex bis-gluconate in 100 mg of 5% mannitol | 3 |
| 2 ml of LuTex diacetate in 100 mg? of _% phosphate buffer | 3 |
| 20 ml of LuTex bis-formate in 2 g of 5% mannitol | 2 |

5C. Efficacy Analysis

The test compounds are compared for efficacy as phototherapeutic agents in cancer. In order to evaluate the effectiveness and determine the optimal drug and light regiment of the various test compounds, each of the test compounds is used as a photodynamic (PDT) agent using the murine EMT6 sarcoma model. The EMT6 tumor cell line, murine mammary sarcoma, (Stanford University, Stanford, Calif.) is maintained through in vivo/in vitro propagation according to the established procedure of Rockwell and Kallman, found in, "Growth and cell Population Kinetics of Single and Multiple KHT Sarcomas" Cell Tissue Kinetics, 1972, 1, pp.449–457. The EMT6 cells ($1\times10^6$) are grown in 50 $\mu$l Waymouth's Medium (MB752/1, GIBCO, Grand Island N.Y.), supplemented with 15% fetal bovine serum (GIBCO, Grand Island N.Y.) and penicillin/streptomycin (Sigma, St. Louis, Mo.). Thirty Two female Balb/c mice weighing 18–22 g and between 10 to 12 weeks old, are obtained from Simonsen Laboratories, Gilroy Calif. The right flanks of the mice are shaved and depiled the day prior to tumor inoculation. The tumor cells ($1\times10^6$ in 0.05 ml Waymouth's Medium) are injected subcutaneously into the right flanks of the recipient mice. The length (l), width (w), and height (h) of the tumor are measured 3 times a week with a vernier caliper. Tumor volume is calculated assuming the conformation of a hemiellipsoid, and following the formula:

$$V=\pi/6\times(1)\times(w)\times(h)$$

Mice are entered into PDT studies when their tumors reached surface diameters of between 5–7 mm and depths of 3–5 mm. The tumors are measured for 40 days post PDT treatment. Each test compound (10 mg/kg) is administered to eight mice by tail-vein injection, and the tumor is irradiated 5 hours later by localized laser irradiation using a ALGaAs diode laser (Diomed Cambridge, UK) at 732 mm. Eight mice used as controls are injected with 10 mg/kg of 5% mannitol but no test compound, and are also irradiated 5 hours post injection by localized laser irradiation at 732 mm. During the laser irradiation, each mouse is restrained with laboratory tape. A 400 $\mu$m diameter fiberoptic cable couples the laser to the microlens which produces uniform light intensity in the treatment field. The light fluences are 100 J/cm$^2$, and the power density is set to 75 mW/cm$^2$. Power measurements are made with a power meter (Scientech Boulder, Co).

When each mouse appears moribund or when the tumor appears to grow to four times the prestudy volume, it is removed from the study. As illustrated in FIG. 3, the number of mice remaining in the study (percent survival) is plotted against the number of days after treatment. The mice are euthanized by either carbon dioxide or methane inhalation.

The different test compounds, number of mice treated and treatment regiments are outlined below.

| Test compound | Number of Mice Treated | Treatment |
|---|---|---|
| 20 ml of 5% mannitol (control) | 8 | 75 m W/cm$^2$ @ 100 J/cm$^2$ |
| 20 ml of LuTex diacetate (2 mg/ml in 5% mannitol) | 8 | 75 m W/cm$^2$ @ 100 J/cm$^2$ |
| 20 ml of LuTex bis-gluconate (2 mg/ml in 5% mannitol) | 8 | 75 m W/cm$^2$ @ 100 J/cm$^2$ |
| 20 ml of LuTex bis-formate (2 mg/ml in 5% mannitol) | 8 | 75 m W/cm$^2$ @ 100 J/cm$^2$ |

The following examples illustrate the preparation of representative pharmaceutical formulations containing a compound of Formula I, such as those prepared in accordance with Example 1.

Example 6

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

Example 7

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Example 8

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Example 9

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Example 10

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

Example 11

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 12

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Example 13

A subcutaneous formulation may be prepared as follows:

| Ingredient | Quantity |
| --- | --- |
| Active Ingredient | 5.0 mg |
| Corn Oil | 1.0 mL |

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472, which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

Example 14

An injectable preparation is prepared having the following composition:

| Ingredients | Amount |
| --- | --- |
| Lu-Tex bis-gluconate | 2.0 mg/ml |
| Mannitol, USP | 50 mg/ml |
| Gluconic acid, USP | q.s. (pH 5–6) |
| water (distilled, sterile) | q.s. to 1.0 ml |
| Nitrogen Gas, NF | q.s. |

Other compounds of Formula I, such as those prepared in accordance with Example 1, can be used as the active compound in the preparation of the injectable formulations of this example.

Example 15

A topical preparation is prepared having the following composition:

| Ingredients | grams |
| --- | --- |
| Lu Tex bis benzoate | 0.2–10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Example 1, can be used as the active compound in the preparation of the topical formulations of this example While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All of the above references are herein incorporated by reference in their entirety to the same extent as if each individual reference was specifically and individually indicated to be incorporated by reference in its entirety.

What is claimed is:

1. A compound of the Formula:

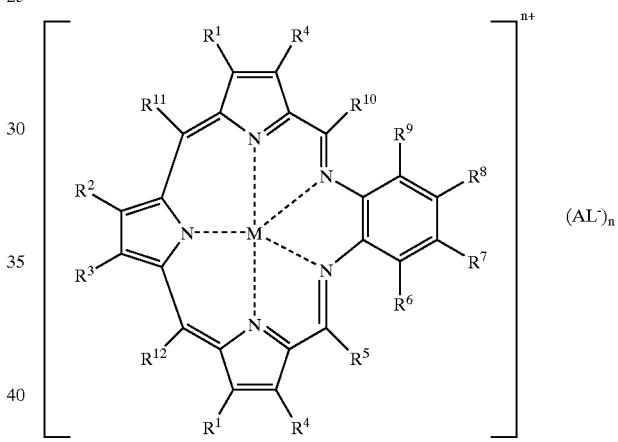

Formula I wherein:
M is a monovalent, divalent, trivalent, or tetravalent metal cation;
AL is an apical ligand;
with the proviso that AL is not derived from acetic acid, nitric acid, or hydrochloric acid;
n is 1 when M is a divalent cation, or n is 2 when M is a trivalent cation;
$R^1$, $R^2$, $R^3$, $R^4$, $R^5$, $R^6$, $R^7$, $R^8$, and $R^9$, are independently chosen from the group consisting of hydrogen, halogen, hydroxyl, optionally substituted alkyl, optionally substituted alkenyl, optionally substituted alkynyl, optionally substituted aryl, optionally substituted heteroaryl, optionally substituted haloalkyl; alkylalkoxy, nitro, acyl, optionally substituted alkoxy, saccharide, optionally substituted amino, carboxyl, optionally substituted carboxyalkyl, optionally substituted carboxyamide, optionally substituted carboxyamidealkyl, optionally substituted heterocycle, optionally substituted cycloalkyl, optionally substituted arylalkyl, optionally substituted heteroarylalkyl, optionally substituted heterocycloalkylalkyl; and a group —X—Y, in which X is a covalent bond or a linker and Y is a catalytic group, a chemotherapeutic agent, or a site-directing molecule, and;

$R^5$, $R^{10}$, $R^{11}$, and $R^{12}$ are independently hydrogen, optionally substituted alkyl, optionally substituted aryl, optionally substituted alkoxy, optionally substituted carboxyalkyl, or optionally substituted carboxyamidealkyl;

with the proviso that the halogen is other than iodide and the haloalkyl is other than iodoalkyl.

2. The compound of claim 1, wherein M is a divalent metal cation chosen from Ca(II), Mn(II), Co(II), Ni(II), Zn(II), Cd(II), Hg(II), Fe(II), Sm(II), and $UO_2$(II), or a trivalent metal cation chosen from Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III),Tm(III), Yb (III), Lu(III), La(III), and U(III).

3. The compound of claim 2, wherein the apical ligand is derived from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

4. The compound of claim 3, wherein:

$R^1 R^2$, $R^3$, and $R^4$ are optionally substituted alkyl of 1–10 carbon atoms, $R^5$, $R^6$, $R^9$, $R^{10}$, $R^{11}$ and $R^{12}$ are hydrogen or alkyl of 1–6 carbon atoms; and $R^7$ and $R^8$ are optionally substituted alkoxy or alkylalkoxy.

5. The compound of claim 4, wherein $R^1$ at each occurrence is hydroxyalkyl, $R^4$ at each occurrence is alkyl, and $R^5$, $R^6$, $R^9$, $R^{10}$, $R^{11}$ and $R^{12}$ are hydrogen.

6. The compound of claim 5, wherein $R^1$ at each occurrence is 2-hydroxyethyl or 3-hydroxypropyl, $R^4$ at each occurrence is methyl or ethyl, and $R^7$ and $R^8$ are both —O(CH$_2$CH$_2$O)$_x$Z, where x is an integer of 2–5, and Z is hydroxy or alkyl of 1–6 carbon atoms.

7. The compound of claim 6, wherein Z is methyl or hydroxy and x is 1–3.

8. The compound of claim 7, wherein M is Lu(III) or or Gd(III) and AL is derived from gluconic acid, glucoronic acid, cholic acid, deoxycholic acid, methylphosphonic acid, phenylphosphonic acid, phosphoric acid, formic acid, benzoic acid, methylvaleric acid, 3,6,9-trioxodecanoic acid, 3,6-dioxoheptanoic acid, or 2,5-dioxoheptanoic acid.

9. The compound of claim 8, wherein $R^1$ is 3-hydroxypropyl, $R^2$ and $R^3$ are ethyl, $R^4$ is methyl, and $R^7$ and $R^8$ are 2-[2-[-(2-methoxyethoxy)ethoxy]ethoxy.

10. The compound of claim 9, wherein M is Lu(III) and the apical ligand is derived from gluconic acid, namely the lutetium (III) complex of: 4,5-diethyl-10,23-dimethyl-9,24-bis(3-hydroxy propyl)-16,17-bis[2-[2-(2 methoxyethoxy) ethoxy]ethoxy]pentaazapentacyclo-[20.2.1.1$^{3,6}$.1$^{8,11}$.0$^{14,19}$] heptacosa-1,3,5,7,9,11(27),12,14,16,18,20,22(25),23-tridecaene bis gluconate.

11. A method for treating a disease or condition in a mammal resulting from the presence of neoplastic tissue, neovascularization, or an atheroma, which method comprises:

a) administering to a mammal in need of such treatment a therapeutically effective amount of a compound of claim 1, and b) treating the area in proximity to the neoplastic tissue with a therapeutic energy means or with a chemotherapeutic agent; or c) treating the area in proximity to the neovascularization or atheroma with a therapeutic energy means.

12. The method of claim 11, wherein the therapeutic energy means is chosen from photoirradiation, ionizing radiation, neutron irradiation, and ultrasound.

13. The method of claim 12, wherein M is a divalent metal cation chosen from Ca(II), Mn(II), Co(II), Ni(II), Zn(II), Cd(II), Hg(II), Fe(II), Sm(II), and $UO_2$(II), or a trivalent metal cation chosen from Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III).

14. The method of claim 13, wherein the apical ligand is derived from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

15. The method of claim 14, wherein:

$R^1 R^2$, $R^3$, and $R^4$ are optionally substituted alkyl of 1–10 carbon atoms, $R^5$, $R^6$, $R^9$, $R^{10}$, $R^{11}$ and $R^{12}$ are hydrogen or alkyl of 1–6 carbon atoms; and $R^7$ and $R^8$ are optionally substituted alkoxy or alkylalkoxy.

16. The method of claim 15, wherein $R^1$ at each occurrence is hydroxyalkyl, $R^4$ at each occurrence is alkyl, and $R^5$, $R^6$, $R^9$, $R^{10}$, $R^{11}$ and $R^{12}$ are hydrogen.

17. The method of claim 16, wherein $R^1$ at each occurrence is 2-hydroxyethyl or 3-hydroxypropyl, $R^4$ at each occurrence is methyl or ethyl, and $R^7$ and $R^8$ are both —O(CH$_2$CH$_2$O)$_x$Z, where x is an integer of 2–5, and Z is hydroxy or alkyl of 1–6 carbon atoms.

18. The method of claim 17, wherein Z is methyl or hydroxy and x is 1–3.

19. The method of claim 18, wherein M is Lu(III) or or Gd(III) and AL is derived from gluconic acid, glucoronic acid, cholic acid, deoxycholic acid, methylphosphonic acid, phenylphosphonic acid, phosphoric acid, formic acid, benzoic acid, methylvaleric acid, 3,6,9-trioxodecanoic acid, 3,6-dioxoheptanoic acid, or 2,5-dioxoheptanoic acid.

20. The method of claim 19, wherein $R^1$ is 3-hydroxypropyl, $R^2$ and $R^3$ are ethyl, $R^4$ is methyl, and $R^7$ and $R^8$ are 2-[2-[-(2-methoxyethoxy)ethoxy]ethoxy.

21. The method of claim 20, wherein M is Lu(III) and the apical ligand is derived from gluconic acid, namely the lutetium (III) complex of: 4,5-diethyl-10,23-dimethyl-9,24-bis(3-hydroxy propyl)-16,17-bis[2-[2-(2 methoxyethoxy) ethoxy]ethoxy]pentaazapentacyclo-[20.2.1.1$^{3,6}$.1$^{8,11}$.0$^{14,19}$] heptacosa-1,3,5,7,9,11(27),12,14,16,18,20,22(25), 23-tridecaene bis gluconate.

22. A pharmaceutical composition comprising at least one pharmaceutically acceptable excipient and a therapeutically effective amount of a compound of claim 1.

23. The composition of claim 22, wherein M is a divalent metal cation chosen from Ca(II), Mn(II), Co(II), Ni(II), Zn(II), Cd(II), Hg(II), Fe(II), Sm(II), and $UO_2$(II), or a trivalent metal cation chosen from Mn(III), Co(III), Ni(III), Fe(III), Ho(III), Ce(III), Y(III), In(II), Pr(III), Nd(III), Sm(III), Eu(III), Gd(III), Tb(III), Dy(III), Er(III), Tm(III), Yb(III), Lu(III), La(III), and U(III).

24. The composition of claim 23, wherein the apical ligand is derived from the group consisting of gluconic acid, glucoronic acid, cholic acid, deoxycholic acid, methylphosphonic acid, phenylphosphonic acid, phosphoric acid, formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

25. The composition of claim 24, wherein:

$R^1$ $R^2$, $R^3$, and $R^4$ are optionally substituted alkyl of 1–10 carbon atoms, $R^5$, $R^6$, $R^9$, $R^{10}$, $R^{11}$ and $R^{12}$ are hydrogen or alkyl of 1–6 carbon atoms; and $R^7$ and $R^8$ are optionally substituted alkoxy or alkylalkoxy.

26. The composition of claim 25, wherein $R^1$ at each occurrence is hydroxyalkyl, $R^4$ at each occurrence is alkyl, and $R^5$, $R^6$, $R^9$, $R^{10}$, $R^{11}$ and $R^{12}$ are hydrogen.

27. The composition of claim 26, wherein $R^1$ at each occurrence is 2-hydroxyethyl or 3-hydroxypropyl, $R^4$ at each occurrence is methyl or ethyl, and $R^7$ and $R^8$ are both $-O(CH_2CH_2O)_xZ$, where x is an integer of 2–5, and Z is hydroxy or alkyl of 1–6 carbon atoms.

28. The composition of claim 27, wherein Z is methyl or hydroxy and x is 1–3.

29. The composition of claim 28, wherein M is Lu(III) or or Gd(III) and AL is derived from gluconic acid, glucoronic acid, cholic acid, deoxycholic acid, methylphosphonic acid, phenylphosphonic acid, phosphoric acid, formic acid, benzoic acid, methylvaleric acid, 3,6,9-trioxodecanoic acid, 3,6-dioxoheptanoic acid, or 2,5-dioxoheptanoic acid.

30. The composition of claim 29, wherein $R^1$ is 3-hydroxypropyl, $R^2$ and $R^3$ are ethyl, $R^4$ is methyl, and $R^7$ and $R^8$ are 2-[2-[-(2-methoxyethoxy)ethoxy]ethoxy.

31. The composition of claim 30, wherein M is Lu(III) and the apical ligand is derived from gluconic acid, namely the lutetium (III) complex of: 4,5-diethyl-10,23-dimethyl-9,24-bis(3-hydroxy propyl)-16,17-bis[2-[2-(2 methoxyethoxy)ethoxy]ethoxy]pentaazapentacyclo-[20.2.1.1$^{3,6}$.1$^{8,11}$.0$^{14,19}$]heptacosa-1,3,5,7,9,11(27),12,14,16,18,20,22(25), 23-tridecaene bis gluconate.

32. A process for preparing a metallotexaphyrin having the formula:

$$(T-M)^{n+}(AL^-)_n$$

wherein:
T is a texaphyrin;
M is a divalent or trivalent metal cation constrained within the binding cavity of the texaphyrin;
AL is an apical ligand; and
n is an integer of 1–5;
comprising:
a) contacting an apical ligand (AL)H with a quarternary amine resin;
b) contacting the resin complex produced in step a) with a metallotexaphyrin of the formula:

$$(T-M)^{n+}(AL_1^-)_n$$

in which T and M are as defined above;
(AL$_1$) represents a displaceable apical ligand; and
n is an integer of 1–5.

33. The process of claim 32, wherein M is Lu(III) or Gd(III), (AL$_1$) is acetate, and n is 2.

34. The process of claim 33, wherein (AL)H is chosen from formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

35. A process for preparing a metallotexaphyrin having the formula:

$$(T-M)^{n+}(AL^-)_n$$

wherein:
T is a texaphyrin;
M is a divalent or trivalent metal cation constrained within the binding cavity of the texaphyrin;
AL is an apical ligand; and
n is an integer of 1–5;
comprising:
contacting a metallotexaphyrin of the formula:

$$(T-M)^{n+}(AL_1^-)_n$$

in which T and M are as defined above;
(AL$_1$) represents a displaceable apical ligand; and
n is an integer of 1–5;
with an excess of an apical ligand (AL)H;
at a temperature of 20–100° C.

36. The process of claim 35, wherein M is Lu(III) or Gd(III), (AL$_1$) is acetate, and n is 2.

37. The process of claim 36, wherein (AL)H is chosen from formic acid, propionic acid, butyric acid, pentanoic acid, 3,6,9-trioxodecanoic acid, 3,6-dioxoheptanoic acid, 2,5-dioxoheptanoic acid, methylvaleric acid, glycolic acid, pyruvic acid, oxalic acid, malic acid, malonic acid, succinic acid, maleic acid, fumaric acid, tartaric acid, citric acid, methanesulfonic acid, ethanesulfonic acid, benzoic acid, salicylic acid, 3-fluorobenzoic acid, 4-aminobenzoic acid, cinnamic acid, mandelic acid, and p-toluene-sulfonic acid.

* * * * *